United States Patent [19]

Shiokawa et al.

[11] Patent Number: 4,880,933

[45] Date of Patent: Nov. 14, 1989

[54] NITRO- OR CYANO-DERIVATIVES OF 2-IMINO-IMIDAZOLINES AND 2-IMINO-TETRAHYDROPYRIMIDINES

[75] Inventors: Kozo Shiokawa, Kawasaki; Shinichi Tsuboi, Hino; Koichi Moriya, Tokyo; Katsuhiko Shibuya, Hachioji, all of Japan

[73] Assignee: Nihon Tokushu Noyaku Seizo K.K., Tokyo, Japan

[21] Appl. No.: 130,376

[22] Filed: Dec. 8, 1987

[30] Foreign Application Priority Data

Dec. 19, 1986 [JP] Japan ................. 61-301333

[51] Int. Cl.$^4$ ............ C07D 233/52; C07D 239/18; C07D 401/06; C07D 417/04; C07D 407/06
[52] U.S. Cl. ................. 544/332; 546/278; 548/110; 548/111; 548/112; 548/190; 548/315
[58] Field of Search ............ 544/232, 330, 331, 332, 544/332; 548/110, 348, 315, 190, 112, 111; 546/278

[56] References Cited

U.S. PATENT DOCUMENTS

| | | | |
|---|---|---|---|
| 2,525,927 | 10/1950 | McKay et al. | 544/298 |
| 4,297,496 | 10/1981 | Davis et al. | 544/332 |
| 4,369,325 | 1/1983 | Toldy et al. | 548/315 |
| 4,574,155 | 3/1986 | Padmanathan | 544/330 |
| 4,590,272 | 5/1986 | Shiokawa et al. | 544/335 |
| 4,742,060 | 5/1988 | Shiokawa et al. | 514/252 |
| 4,803,227 | 2/1989 | Shiokawa et al. | 514/252 |

FOREIGN PATENT DOCUMENTS

| | | |
|---|---|---|
| 0235725 | 9/1987 | European Pat. Off. . |
| 2205745 | 8/1973 | Fed. Rep. of Germany . |
| 91064 | 11/1973 | Japan . |
| 2055796 | 3/1981 | United Kingdom . |

OTHER PUBLICATIONS

Davis et al., CA 96–69023j, (1982), "2–Nitriminohexahydropyrimidines".
Shiokawa et al., CA 106–28848p, (1987), "Heterocyclic Compounds".
Shiokawa et al., CA 108–21897m, (1988), "Preparation of (Heterocyclylmethyl)imidazolines . . . ".
Tsuboi et al., CA 109–124423d, (1988), "Agricultural Insecticide . . . ".
Manfred et al., CA 78–84373v, (1973).
Heinemann, CA 76–122673m, (1972).
Barton et al., JACS 73; pp. 2201-2205, (1951).
Toldy et al., CA 92–181226w, (1980), "1,3-Diphenyl-2-Iminoimidazolidines and 1,3-Diphenyl . . . ".
Chemical & Pharmaceutical Bullentin, Band 27, No. 4.
Chemical & Pharmaceutical Bullentin, Band 26, No. 12, 3658-3674.
European Search Report.
Can. J. Chem., vol. 39, pp. 1978 to 1796.

*Primary Examiner*—Cecilia Shen
*Attorney, Agent, or Firm*—Sprung Horn Kramer & Woods

[57] ABSTRACT

Novel intermediates for insecticides of the formula (I)

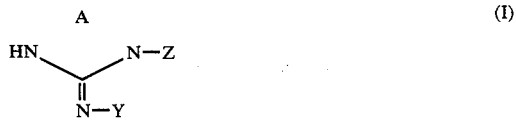

wherein
Y represents nitro or cyano;
A represents an ethylene or trimethylene radical, which is optionally substituted; and
Z can have many possible meanings.

2 Claims, No Drawings

NITRO- OR CYANO-DERIVATIVES OF 2-IMINO-IMIDAZOLINES AND 2-IMINO-TETRAHYDROPYRIMIDINES

The present invention relates to novel nitro- or cyanoimino compounds and to processes for their preparation.

It has already been disclosed that certain cyanoimino compounds are useful as intermediates for active compounds such as insecticides, anti-diabetic agents, virus-suppressing agents and diuretic agents (see Japanese patent Laid-open 91,064/1983).

Furthermore, certain nitroimino compounds have been disclosed in Can. J. Chem., Vol. 39, pp. 1787 to 1796.

There have now been found novel-nitro- or cyano derivatives of 2-imino-imidazolidines and 2-imino-tetrahydropyrimidines of the general formula (I):

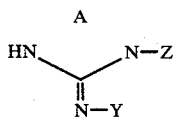

(I)

wherein Y represents nitro or cyano;

A represents an ethylene or trimethylene radical, which is optionally mono- or poly-substituted (e.g. di- or tri-substituted) with one or more radicals selected, for instance, from the class consisting of halogen and alkyl with 1 to 4 carbon atoms;

Z represents cycloalkyl with 3 to 7 carbon atoms (which is optionally substituted with methyl);
haloalkyl with 1 to 4 carbon atoms;
alkoxyalkyl having 2 to 6 carbon atoms in total;
alkylthioalkyl having 2 to 6 carbon atoms in total;
alkylsulfinylalkyl having 2 to 6 carbon atoms in total;
alkylsulfonylalkyl having 2 to 6 carbon atoms in total;
alkyl having 1 to 3 carbon atoms and carrying one or more substituents (which substituents are selected, for instance, from the class consisting of optionally substituted phenoxy, optionally substituted phenylthio, optionally substituted pyridyloxy, optionally substituted cycloalkyl having 3 to 6 carbon atoms, optionally substituted pyridylthio, thiazolylthio, benzyloxy, thiocyanato, dialkylamino having 2 to 6 carbon atoms in total, alkoxy-alkoxy having 2 to 4 carbon atoms in total, optionally substituted anilino, optionally substituted pyridylamino, cyano, alkylcarbonyl having an alkyl moiety with 2 to 4 carbon atoms, optionally substituted benzoyl, haloalkylcarbonyl with a haloalkyl moiety having 1 to 3 carbon atoms, pyridylcarbonyl, alkoxycarbonyl having an alkyl moiety with 1 to 4 carbon atoms, optionally substituted phenoxycarbonyl, benzyloxycarbonyl, carbamoyl, alkylaminocarbonyl with 1 to 3 carbon atoms, dialkylaminocarbonyl having 2 to 6 carbon atoms in total, optionally substituted phenylaminocarbonyl, hydroxy, alkylcarbonyloxy with 1 to 3 carbon atoms (which is optionally substituted with halogen), benzoyloxy, alkylsulfonyloxy with 1 to 4 carbon atoms, tosyloxy, dialkylaminocarbonyloxy having an alkyl moiety with 1 to 3 carbon atoms, a phosphate ester radical, a thiophosphate ester radical, an amidothiophosphate radical, trimethylsilyl, an optionally substituted 9- or 10-membered condensed heterocyclic radical having at least one hetero-atom selected from the group consisting of N, O and S);

phenyl (which may optionally carry one or more substituents selected, for instance, from the class consisting of halogen, alkyl with 1 to 3 carbon atoms, and nitro);
a 5- or 6-membered heterocyclic or 9- or 10-membered condensed heterocyclic radical having at least one hetero-atom selected from the group consisting of N, O and S (which is optionally substituted with a radical as in the above phenyl group);
alkenyl having 3 to 4 carbon atoms optionally substituted with halogen;
propargyl optionally substituted with halogen;
alkoxyl with 1 to 4 carbon atoms; cyano; phenoxy; benzyloxy; alkenyloxy with 2 or 3 carbon atoms;
alkylthio with 1 to 4 carbon atoms optionally substituted with halogen;
phenylthio optionally substituted with halogen and/or alkyl having 1 to 4 carbon atoms;
halobenzylthio; dialkylamino having 2 to 6 carbon atoms in total;
alkylcarbonyl having an alkyl moiety with 2 to 6 carbon atoms;
alkylcarbonyl having an alkyl moiety with 1 to 4 carbon atoms having a substituent (which is selected, for instance, from the group consisting of halogen, alkoxy with 1 to 4 carbon atoms, alkylthio with 1 to 4 carbon atoms, alkylcarbonyloxy having an alkyl moiety with 1 to 4 carbon atoms, halophenoxy, phenyl, cyano, and alkylcarbonyl having an alkyl moiety with 1 to 2 carbon atoms);
cycloalkylcarbonyl with 3 to 6 carbon atoms optionally substituted with halogen and/or with alkyl having 1 to 4 carbon atoms;
benzoyl (which may be optionally substituted, for instance, with a radical selected from the group consisting of halogen, alkyl with 1 to 4 carbon atoms, alkoxy with 1 to 4 carbon atoms, nitro, haloalkyl with 1 to 4 carbon atoms, alkylcarbonylamino having an alkyl moiety with 1 to 4 carbon atoms, and alkoxy-alkoxy having 2 to 4 carbon atoms in total);
alkenylcarbonyl having an alkenyl moiety with 2 to 4 carbon atoms optionally substituted with halogen;
alkynylcarbonyl having an alkynyl moiety with 2 to 3 carbon atoms;
a radical of the formula:

(wherein $U^2$ represents a 5- or 6-membered heterocyclic or 9- or 10-membered condensed heterocyclic radical having at least one hetero-atom selected from the group consisting of N, O and S (which heterocyclic radical may optionally carry one or more substituents selected, for example, from the group consisting of halogen, alkyl with 1 to 4 carbon atoms, haloalkyl with 1 to 4 carbon atoms, phenyl, nitro, alkylthio with 1 to 4 carbon atoms, and oxo);
alkoxycarbonyl having an alkyl moiety with 1 to 3 carbon atoms substituted with a radical (which substituent is selected, for instance, from the group consisting of halogen, alkoxy with 1 or 2 carbon atoms, alkylthio with 1 to 2 carbon atoms, dialkylamino having 2 to 4 carbon atoms in total, hydroxy, and halophenoxy);
cycloalkoxycarbonyl having a cycloalkyl moiety with 3 to 7 carbon atoms (which may be optionally substituted with alkyl having 1 to 4 carbon atoms);

phenoxycarbonyl substituted with a radical (which substituent is selected, for instance, from the group consisting of halogen, alkyl with 1 to 4 carbon atoms, haloalkyl with 1 to 4 carbon atoms, cyano, alkylthio with 1 to 4 carbon atoms, alkoxy with 1 to 4 carbon atoms, nitro, alkylsulfinyl with 1 to 4 carbon atoms, alkoxycarbonyl having an alkyl moiety with 1 to 4 carbon atoms, and pyridyloxy substituted with halogen and/or with trihaloalkyl);

benzyloxycarbonyl optionally substituted with a radical (which substituent is selected, for instance, from the class consisting of halogen, haloalkyl with 1 to 2 carbon atoms, alkoxy with 1 to 4 carbon atoms, and phenoxy);

phenylthiocarbonyl; alkylthiocarbonyl having an alkyl moiety with 1 to 4 carbon atoms; alkenyloxycarbonyl having an alkenyl moiety with 2 to 4 carbon atoms optionally substituted with halogen; alkynyloxycarbonyl having an alkynyl moiety with 2 to 4 carbon atoms optionally substituted with halogen;

a radical of the formula:

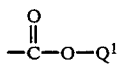

(wherein $Q^1$ represents a 5- or 6-membered heterocyclic or 9- or 10-membered condensed heterocyclic radical having at least one hetero-atom selected from the group consisting of N, O and S, which is optionally substituted with a radical selected, for instance, from the group consisting of halogen, alkyl with 1 to 4 carbon atoms, phenyl, oxo and haloalkyl with 1 to 4 carbon atoms);

carbomoyl; alkylaminocarbonyl having an alkyl moiety with 1 to 4 carbon atoms; cycloalkylaminocarbonyl having a cycloalkyl moiety with 3 to 6 carbon atoms;

phenylaminocarbonyl (which may be optionally substituted with a radical selected, for example, from the group consisting of halogen, alkyl with 1 to 4 carbon atoms, and alkoxy with 1 to 4 carbon atoms);

dialkylaminocarbonyl having alkyl moieties with 2 to 8 carbon atoms in total;

a radical of the formula:

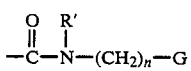

(wherein G represents a 5- or 6-membered heterocyclic or 9- or 10-membered condensed heterocyclic radical having at least one hetero-atom selected from the class consisting of N, O and S, which is optionally substituted with a radical selected, for instance, from the group consisting of halogen, alkyl with 1 to 4 carbon atoms, alkoxy with 1 to 4 carbon atoms, haloalkyl with 1 to 4 carbon atoms, and alkylsulfonyl with 1 or 2 carbon atoms;

n is 0 or 1; and

R' represents hydrogen or alkyl with 1 to 4 carbon atoms);

piperidinocarbonyl which is optionally substituted, for instance, with alkyl having 1 to 4 carbon atoms;

morpholinocarbonyl which is optionally substituted, for instance, with alkyl having 1 to 4 carbon atoms;

pyrrolidinocarbonyl;

benzylaminocarbonyl optionally substituted with methyl;

mono- or di-alkenylaminocarbonyl having one or two alkenyl moieties with 2 to 3 carbon atoms;

alkynylamino-carbonyl with a alkynyl moiety having 2 to 3 carbon atoms;

alkylsulfonyl with 1 to 4 carbon atoms (which radical may be optionally substituted with halogen);

phenylsulfonyl (which may be optionally substituted with a radical selected, for instance, from the group consisting of halogen, alkyl with 1 to 4 carbon atoms, and nitro);

alkoxysulfonyl with 1 to 4 carbon atoms;

cycloalkoxysulfonyl with 3 to 6 carbon atoms;

mono- or di-($C_{1-4}$ alkyl)-aminosulfonyl;

phenylaminocarbonyl (which may be optionally substituted with methyl);

O,O-di-($C_{1-4}$ alkyl)-phosphono;

O,O-di-($C_{1-4}$ alkyl)-thiophosphono;

O,S-di-($C_{1-4}$ alkyl)-thiophosphono;

O-($C_{1-4}$ alkyl)-O-(phenyl optionally substituted with halogen)thiophosphono;

O,N-di-($C_{1-4}$ alkyl)-amidothiophosphono;

alkoxalyl with 1 to 4 carbon atoms;

phenoxalyl optionally substituted with halogen;

benzyloxalyl; or a radical of the formula

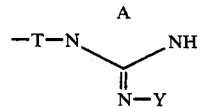

wherein Y and A have the meanings stated above, and T represents —S—, —S—S—,

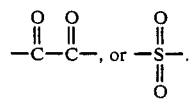

The compounds of the formula (I) are obtained by a process in which, (a) compounds of the formula (II)

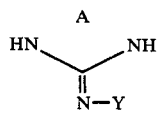

wherein Y and A have the meanings stated above, are reacted with compounds of the formula (III)

  (III)

wherein Z has the meaning stated above, and $M^1$ represents halogen, preferably chlorine or bromine, in the presence of an inert solvent and if appropriate in the presence of a base, or (b) compounds of the formula (IV)

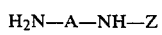  (IV)

wherein A and Z have the meanings stated above, are reacted with compounds of the formula (V)

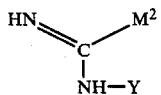

wherein Y has the meaning stated above, and $M^2$ represents amino, alkylthio or benzylthio, in the presence of an inert solvent, or (c) in the case where Y is cyano:
compounds of the aforesaid formula (IV) are reacted with compounds of the formula (IV)

wherein $M^3$ represents alkylthio or benzylthio, with the proviso that the two radicals $M^3$, together with the sulfur atoms, may form a ring, in the presence of an inert solvent.

The novel nitro- or cyano imino compounds are very useful as intermediates for certain insecticidal nitro- or cyano-imino compounds as stated in detail hereinafter.

Among the compounds of the formula (I) according to the invention, of the formula (I), preferred compounds are those in which Y represents nitro or cyano;

A represents an ethylene or trimethylene radical, which may optionally mono- or di-substituted (e.g. di- or tri-substituted) with chlorine or methyl;

Z represents cycloalkyl with 5 to 6 carbon atoms (which is optionally substituted with methyl);
haloalkyl with 1 to 3 carbon atoms;
alkoxyalkyl having 2 to 4 carbon atoms in total;
alkylthioalkyl having 2 to 4 carbon atoms in total;
alkylsulfinylalkyl having 2 to 4 carbon atoms in total;
alkylsulfonylalkyl having 2 to 4 carbon atoms in total;
alkyl having 1 to 3 carbon atoms and carrying one or more substituents [(which substituents are selected from phenoxy optionally substituted with at least one member selected from halogen, nitro, alkyl with 1 to 4 carbon atoms, haloalkyl with 1 to 4 carbon atoms and haloalkoxy with 1 to 4 carbon atoms);
phenylthio optionally substituted with at least one radical such as shown in the above phenoxy group;
pyridylthio optionally substituted with a halogen;
cycloalkyl with 3 to 7 carbon atoms optionally substituted with chlorine and/or methyl; pyridylthio optionally substituted with a halogen;
thiazolylthio; benzyloxy; thiocyanato; dialkylamino having 2 to 4 carbon atoms in total; alkoxy-alkoxy having 2 to 3 carbon atoms in total;
anilino optionally substituted with at least one radical selected from halogen and alkyl with 1 to 4 carbon atoms; pyridylamino optionally substituted with at least one radical such as shown in the above anilino group; cyano;
alkylcarbonyl having an alkyl moiety with 2 to 3 carbon atoms;
benzoyl optionally substituted with a halogen; haloalkylcarbonyl with a haloalkyl moiety having 1 to 2 carbon atoms;
pyridylcarbonyl; alkoxycarbonyl having an alkyl moiety with 1 to 2 carbon atoms;
phenoxycarbonyl optionally substituted with at least one radical selected from halogen and alkyl with 1 to 4 carbon atoms; benzyloxycarbonyl; carbamoyl; alkylaminocarbonyl having an alkyl moiety with 1 to 2 carbon atoms; dialkylaminocarbonyl having an alkyl moiety with 2 to 4 carbon atoms in total; phenylaminocarbonyl; hydroxy; alkylcarbonyloxy with 1 to 2 carbon atoms (which may be optionally substituted with halogen); benzoyloxy; alkylsulfonyloxy with 1 to 2 carbon atoms; tosyloxy; dialkylaminocarbonyloxy having an alkyl moiety with 2 to 4 carbon atoms in total;
O,O-dialkylphosphono with 2 to 6 carbon atoms in total;
O,O-dialkylthiophosphorylthio with 2 to 6 carbon atoms in total;
O,S-dialkylthiophosphoryloxy with 2 to 6 carbon atoms in total;
trimethylsilyl; and a 9- or 10-membered condensed heterocyclic radical with at least one hetero-atom selected from the class consisting of N,O and S (which may be optionally substituted with at least one radical selected from halogen, alkyl with 1 to 4 carbon atoms, haloalkyl with 1 to 4 carbon atoms, phenyl, nitroimino, cyanoimino, oxo, alkylthio with 1 to 4 carbon atoms, and alkoxy with 1 to 4 carbon atoms)];

phenyl (which may optionally carry at least one substituents selected from fluorine, chlorine, bromine methyl, ethyl and nitro);

a 5- or 6-membered heterocyclic or 9- or 10-membered condensed heterocyclic radical having at least one hetero-atom selected from the group consisting of N, O and S (which may be optionally substituted with at least one radical such as shown in the above phenyl group);

alkenyl having 3 to 4 carbon atoms optionally substituted with chlorine;

propargyl optionally substituted with chlorine;

alkoxy with 1 to 4 carbon atoms; cyano; phenoxy; benzyloxy;

vinyloxy; allyloxy;

alkylthio with 1 to 3 carbon atoms optionally substituted with fluorine or chlorine;

phenylthio optionally substituted with at least one radical selected from fluorine, chlorine, methyl and ethyl;

halobenzylthio; dialkylamino having 2 to 4 carbon atoms in total;

alkylcarbonyl having an alkyl moiety with 2 to 4 carbon atoms;

alkylcarbonyl having an alkyl moiety with 1 to 2 carbon atoms having a substituent (which is selected from halogen, alkoxy with 1 to 3 carbon atoms, alkylthio with 1 to 3 carbon atoms, alkylcarbonyloxy having an alkyl moiety with 1 to 3 carbon atoms, halophenoxy, phenyl, cyano, and acetyl);

cycloalkylcarbonyl with 5 to 6 carbon atoms optionally substituted with chlorine and/or methyl;

benzoyl (which may be optionally substituted with at least one radical selected from halogen, alkyl with 1 to 3 carbon atoms, alkoxy with 1 to 3 carbon atoms, nitro, haloalkyl with 1 to 3 carbon atoms, alkylcarbonylamino having an alkyl moiety with 1 to 3 carbon atoms, and alkoxy-alkoxy having 2 to 3 carbon atoms in total);

alkenylcarbonyl having an alkenyl moiety with 2 to 3 carbon atoms optionally substituted with fluorine or chlorine; propargylcarbonyl;

a radical of the formula:

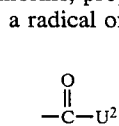

(wherein U² represents a 5- or 6-membered heterocyclic or 9- or 10-membered condensed heterocyclic radical having at least one hetero-atom selected from the group consisting of N, O and S (which heterocyclic radical may optionally carry at least one substituent selected, from fluorine, chlorine, methyl, ethyl, haloalkyl with 1 to 2 carbon atoms, phenyl, nitro, alkylthio with 1 to 2 carbon atoms, and oxo);

alkoxycarbonyl having an alkyl moiety with 1 to 2 carbon atoms substituted with at least one substituent selected from fluorine, chlorine, methoxy, ethylthio, diethylamino, hydroxy and chlorophenoxy);

cycloalkoxycarbonyl having a cycloalkyl moiety with 5 to 6 carbon atoms (which may be optionally substituted with methyl);

phenoxycarbonyl substituted with a radical (which substituent is selected from chlorine, methyl, trifluoromethyl, cyano, methylthio, methoxy, nitro, alkoxycarbonyl having an alkyl moiety with 1 to 3 carbon atoms, and pyridyloxy substituted with chlorine and/or trifluoromethyl);

benzyloxycarbonyl optionally substituted with a radical (which substituent is selected from chlorine, trifluoromethyl, methoxy and phenoxy);

phenylthiocarbonyl; ethylthiocarbonyl; alkenyloxycarbonyl having an alkenyl moiety with 2 to 3 carbon atoms optionally substituted with chlorine; propargyloxycarbonyl optionally substituted with halogen;

a radical of the formula:

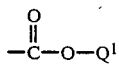

(wherein Q¹ represents a 5- or 6-membered heterocyclic or 9- or 10-membered condensed heterocyclic radical having at least one hetero-atom selected from the group consisting of N, O and S, which may be optionally substituted with a radical selected from chlorine, alkyl with 1 to 3 carbon atoms, phenyl, oxo and trifluoromethyl);

carbamoyl; alkylaminocarbonyl having an alkyl moiety with 1 to 3 carbon atoms; cyclohexylaminocarbonyl;

phenylaminocarbonyl (which is optionally substituted with a radical selected from chlorine, methyl, ethyl, and alkoxy with 1 to 3 carbon atoms);

dialkylaminocarbonyl having alkyl moieties with 2 to 4 carbon atoms in total;

a radical of the formula:

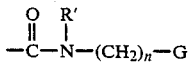

(wherein G represents a 5- or 6-membered heterocyclic or 9-or 10-membered condensed heterocyclic radical having at least one hetero-atom selected from the class consisting of N, O and S, which may be optionally substituted with a radical selected from fluorine, chlorine, alkyl with 1 to 3 carbon atoms, methoxy, trifluoromethyl, and ethylsulfonyl;

n is 0 or 1; and

R¹ represents hydrogen or alkyl with 1 to 3 carbon atoms);

piperidinocarbonyl which may be optionally substituted with methyl;

morpholinocarbonyl which may be optionally substituted with methyl;

pyrrolidinocarbonyl;

benzylaminocarbonyl optionally substituted with methyl; mono- or di-allylaminocarbonyl;

propargylaminocarbonyl;

alkylsulfonyl with 1 to 4 carbon atoms (which may be optionally substituted with chlorine or fluorine);

phenylsulfonyl (which may be optionally substituted with a radical selected from chlorine, methyl and nitro);

methoxysulfonyl;

cyclohexyloxy sulfonyl with 3 to 6 carbon atoms;

mono- or di-($C_{1-3}$ alkyl)-aminosulfonyl;

phenylaminocarbonyl;

O,O-di-($C_{1-3}$ alkyl)-phosphono;

O,O-di-($C_{1-3}$ alkyl)-thiophosphono;

O,S-di-($C_{1-3}$ alkyl)-thiophosphono;

O-($C_{1-2}$ alkyl)-O-(phenyl optionally substituted with chlorine)thiophosphono;

O,N-di-($C_{1-3}$ alkyl)-amidothiophosphono;

alkoxalyl with 1 to 2 carbon atoms;

phenoxalyl optionally substituted with chlorine)benzyloxalyl; or a radical of the formula

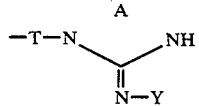

wherein Y and A have the same preferred meanings stated above, and T represents —S—, —S—S—,

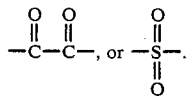

Specifically, the following compounds may be mentioned:

1-cyclopropyl-2-nitroiminoimidazolidine,
1-(2-chloroethyl)-2-nitroiminoimidazolidine,
1-[2-(4-chlorophenoxy)ethyl]-2-nitroiminoimidazolidine,
1-(3-methylthiopropyl)-2-nitroiminoimidazolidine,
1-(2-cyanoethyl)-2-nitroiminoimidazolidine,
1-(3-cyanopropyl)-2-cyanoiminoimidazolidine,
1-(3,3-dimethyl-2-butanon-1-yl)-2-cyanoiminoimidazolidine,
1-(3,3-dimethyl-2-butanon-1-yl)-2-nitroiminoimidazolidine,
2-nitroimino-1-(3-pyridylcarbonylmethyl)imidazolidine,
2-cyanoimino-1-ethoxycarbonylmethyltetrahydropyrimidine,
1(2-hydroxyethyl)-2-nitroiminoimidazolidine,
1-[2-(O-ethyl-S-propylthiophosphonoxy)ethyl]-2-nitroiminoimidazolidine,
2-nitroimino-1-trimethylsilylmethylimidazolidine,
1-(4nitrophenyl)-2-nitroiminoimidazolidine,
2-nitroimino-1-(2-thiazolyl)imidazolidine,
2-nitroimino-1-propylcarbonylimidazolidine,
2-cyanoimino-1-cyclopropylcarbonyltetrahydropyrimidine,
1-bromoacetyl-2-nitroiminoimidazolidine,
2-cyanoimino-1-trichloroacryloylimidazolidine, 1-(2-methoxyethoxycarbonyl)-2-nitroiminoimidazolidine,
1-benzyloxycarbonyl-2-nitroiminoimidazolidine,
1-ethylaminocarbonyl-2-nitroiminoimidazolidine,
1-dimethylaminocarbonyl-2-nitroiminoimidazolidine,
1-methylsulfonyl-2-nitroiminoimidazolidine,
2-nitroimino-1-phenylsulfonyltetrahydropyrimidine,
1-(O,O-dimethylphosphono)-2-nitroiminoimidazolidine,
1-(O-ethyl-S-propylthiophosphono)-2-nitroiminoimidazolidine,
1-(2,4-dichlorobenzoyl)-2-nitroiminoimidazolidine,
1-(3,5-dichlorobenzoyl)-2-cyanoiminoimidazolidine,
1-(2-furoyl)-2-nitroiminoimidazolidine, If, for example in the process (a), 2-nitroiminoimidazolidine and 1-chloro-3,3-dimethyl-2-butanone are used as starting materials, the course of the reaction can be represented by the following equation:

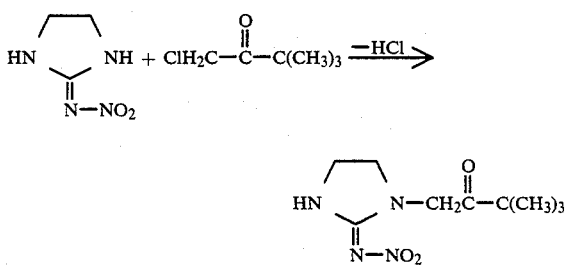

If, for example in the process (b), N-allylethylenediamine and N-nitro S-methylisothiourea are used as starting material, the course of the reaction can be represented by the following equation:

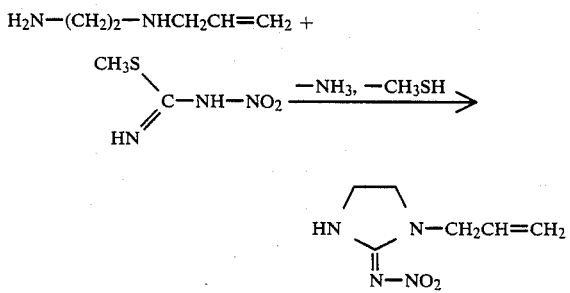

If, for example in the process (c), N-2-phenoxyethylethylenediamine and dimethyl N-cyanodithioiminocarbonate are used as starting materials, the course of the reaction can be represented by the following equation:

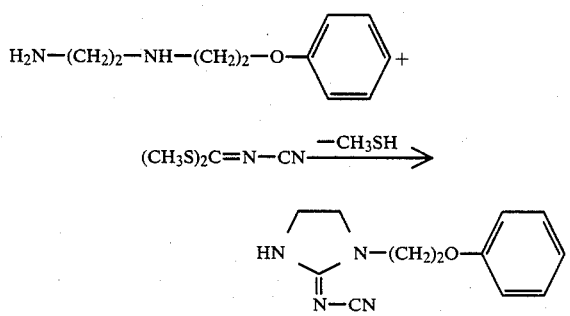

In the process (a), the compounds of the formula (II) as starting materials means those, based on the aforementioned definitions of Y and A.

In the formula (II), Y and A preferably have the meaning already given above.

The compounds of the formula (II) include known ones and are, for instance, described in J. Am. Chem. Soc., Vol. 73, pp. 2201 to 2205, and British Pat. No. 2,055,796.

In the process (a), the compounds of the formula (III) mean those, based on the aforementioned definitions of Z and $M^1$.

In the formula (III), Z and $M^1$ preferably have the meanings already given above.

The compounds of the formula (III) are well known in the field of organic chemistry.

In the process (b), the compounds of the formula (IV) as starting materials mean those based on the aforementioned definitions of A and Z.

In the formula (IV), A and Z preferably have the meanings already given above.

The compounds of the formula (IV) include known ones and in general, are easily obtained when compounds of the formula (VII)

$$H_2N-A-NH_2 \qquad (VII)$$

wherein A has the meaning stated above,
are reacted with the compounds of the aforementioned formula (III) in the presence of an inert solvent and if appropriate in the presence of a base.

The compounds of the above formula (VII) are known.

As examples there may be mentioned: ethylenediamine and trimethylenediamine, described in German Offenlegungsschrift No. 2,732,660 or French Pat. No. 1,499,785.

In the process (b), the compounds of the formula (V) also used as starting materials are known (for instance, see J. Am. Chem. Soc., Vol. 76, p. 1877).

In the process (c), the compounds of the formula (VI) as materials are known from J. Org. Chem., Vo. 32, pp. 1566-1572.

The process (a) according to the invention may be carried out using a suitable solvent or diluent. Virtually any inert organic solvent can be used as the solvent or diluent. Examples of the solvents or diluents are water; aliphatic, cycloaliphatic and aromatic, optionally chlorinated, hydrocarbons, such as hexane, cyclohexane, petroleum ether, ligroin, benzene, toluene, xylene, methylene chloride, chloroform, carbon tetrachloride, ethylene chloride, trichloroethylene, chlorobenzene and the like; ethers such as diethyl ether, methyl ethyl ether, di-isopropyl ether, dibutyl ether, propylene oxide, dioxane, tetrahydrofuran and the like; nitriles such as acetonitrile, propionitrile, acrylonitrile and the like; alcohols such as methanol, ethanol, iso-propanol, butanol, ethylene glycol and the like; acid amides such as dimethyl formamide, dimethyl acetamide and the like; and sulfones and sulfoxides such as dimethyl sulfoxide, sulfolane and the like.

The process (a) according to the invention may be conduct in the presence of a base such as alkali metal hydroxides or carbonates, for instance, sodium hydroxide, potassium hydroxide or the like.

The reaction temperature can be varied within a wide range. In general, the reaction is carried out at a temperature of about 0° to 100° C., preferably about 10° to 80° C.

In general, the reaction is allowed to proceed under normal pressure, although it is also possible to employ a higher or lower pressure.

When the process (a) is carried out in an inert solvent to prepare the compounds of the formula (I), it is possible to use about 0.9 to 1.1 moles of the compounds (II) per 1 mole of the compounds (II) in the presence of a base.

In carrying out the processes (b) and (c), suitable diluents include the same solvents as exemplified for process (a).

Process (b) can generally be conducted at a temperature of about 0° to 120° C., preferably about 30° to 100° C. It is advantageous to carry out the process (b) under normal pressure, although it is also possible to conduct this process under higher or lower pressure.

When the process (b) is carried out to obtain the compounds of the formula (I), generally about 1 to 1.2 moles, preferably about 1 to 1.1 moles of the compounds (V) are used per 1 mole of the compounds (IV). In the process (b), the compounds (IV) and the compounds (V) may be heated, for example, in water to react them with each other.

The process (c) can be carried out, for instance, at a temperature of about 0° C. to the boiling point of the reaction mixture, preferably at a temperature of about 0° to 100° C. It is generally advantageous to conduct the reaction under normal pressure, although a higher or lower pressure may also be employed.

When the process (c) is conducted to obtain the compounds (I), use is made of about 1 to 1.2 moles, preferably about 1 to 1.1 moles of the compounds (VI) per 1 mole of the compounds (IV). This reaction should preferably be conducted in an inert solvent such as an alcohol, e.g. methanol or ethanol until the evolution of mercaptants has ceased.

The compounds of the following formula (E) which can be prepared by using the compounds of the formula (I) as intermediates exhibit strong insecticidal action:

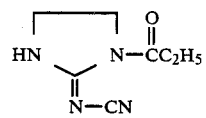

wherein Y, A and Z have the same meanings as stated above, and R represents hydrogen or alkyl, and W represents an optionally substituted 5 or 6-membered heterocyclic radical having at least one hetero-atom and selected from the class consisting of N, O and S.

The preparation of products having formula (E) can be illustrated as follows:

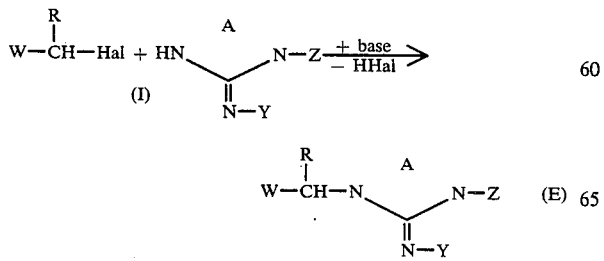

In the above formulae Y, A, Z, W, R have the meanings indicated above and Hal stands for a halogen atom.

The compounds of the above formula (E) can be obtained, for example, in accordance with Referential examples 1 and 2 as specified hereinafter.

Furthermore, the compounds of the formula (I) per se also exhibit an insecticidal action.

The invention is illustrated in detail by the following nonlimiting Examples.

Preparative Examples

Example 1

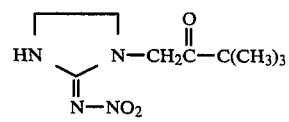

A mixture of 2.6 g of 2-nitroimino-imidazolidine, 3.0 g of anhydrous potassium carbonate and 30 ml of dry acetonitrile was stirred at room temperature for 30 minutes. Then, 2.7 g of 1-chloro-3,3-dimethyl-2-butanone were added to the mixture under stirring at room temperature. The reaction mixture was heated and refluxed for 1 hour. The acetonitrile was distilled off under a reduced pressure, and the residue was admixed with water. The aimed product was separated by filtration. The crystalline product was washed in ether and dried. 3.5 g of 1-(3,3-dimethyl-2-butanon-1-yl)-2-nitroimino-imidazolidine were obtained. mp. 158°–159° C.

Example 2

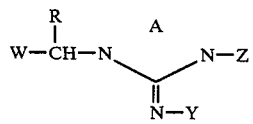

2.2 g of 2-cyanoimino-imidazolidine is dissolved in 20 ml of dry dimethyl formamide. To this solution were portionwise added 1.7 g of 60% oil dispersed sodium hydride at a temperature of at most 0° C. The reaction mixture was stirred at 0° C. until the evolution of hydrogen had ceased. To the reaction mixture were dropwise added 1.9 g of propionyl chloride while the reaction mixture was kept at a temperature lower than 0° C. After this addition, the reaction mixture was stirred at room temperature for a short period of time. The reaction mixture was poured into ice water, and neutralized with hydrochloric acid. An extraction operation was carried out by using dichloromethane, and the extractant was concentrated, so that the aimed product was precipitated as a crystalline material. The precipitated product was separated by filtration, and washed in ether, 1.4 g of 2-cyanoimino-1-propionyl-imidazolidine were obtained. mp. 208°–210° C.

Example 3

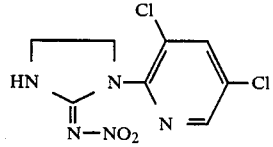

To a solution of 2.6 g of 2-nitroimino-imidazolidine in 20 ml of dimethyl formamide was portionwise added 0.8 g of 60% oil dispersed sodium hydride at room temperature. The reaction mixture was then stirred, until the evolution of hydrogen has ceased. Then, 3.6 g of 2,3,5-trichloropyridine were added, and the reaction mixture was stirred at a temperature of 100° to 120° C. for 7 hours. The reaction was cooled to room temperature, and poured into ice water. The aimed crystalline product thus formed was separated by filtration, and washed with a small amount of ethanol and ether. Yield: 2.2 g; mp. 151°–155° C.

Example 4

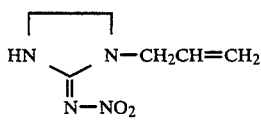

A mixture of 2 g of N-allyl-ethylenediamine ("J. Am. Chem. Soc.", Vol. 67, pages 1581–1582), 2.7 g of N-nitro-S-methyl-isothiourea and 20 ml of ethanol was stirred at 60° C. for 3 hours. The reaction mixture was allowed to cool to room temperature. The aimed crystalline product thus formed was separated by filtration, and washed with a small amount of ethanol, and dried. Yield: 1.4 g; mp. 86°–90° C.

Example 5

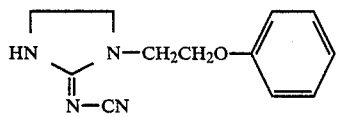

A solution of 3.6 g of N-2-phenoxyethyl-ethylenediamine and 2.9 g of dimethyl-N-cyano-dithioimino-carbonate in 50 ml of ethanol was slowly heated under stirring, and refluxed until the evolution of methyl mercaptane had ceased. After the completion of the reaction, about ⅔ volume of the ethanol was distilled off, and the residue was cooled, so that the aimed crystalline product was formed. The product was separated by filtration, and then dried. Yield: 3.6 g; mp. 93°–95° C.

Furthermore, various compounds of the formula:

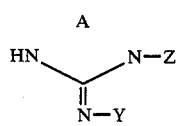 (I)

can be prepared by the same methods as those shown in Examples 3 to 7. These compounds are shown in Table 1.

TABLE 1

| Compound | Y | A | Z | Physical constant |
|---|---|---|---|---|
| 1 | nitro | —CH$_2$CH$_2$— | cyclopropyl | |
| 2 | nitro | —(CH$_2$)$_3$— | cyclopentyl | |
| 3 | cyano | —CH$_2$CH$_2$— | cyclohexyl | |
| 4 | nitro | —CH$_2$CH$_2$— | 4-methyl-cyclohexyl | |
| 5 | nitro | —CH$_2$CH$_2$— | cyclopropylmethyl | |
| 6 | nitro | —CH$_2$CH$_2$— | 2,2-dichloro-3,3-dimethyl-cyclopropylmethyl | |
| 7 | cyano | —(CH$_2$)$_3$— | cyclohexylmethyl | |
| 8 | nitro | —CH$_2$CH$_2$— | difluoromethyl | |
| 9 | nitro | —(CH$_2$)$_3$— | trifluoromethyl | |
| 10 | nitro | ─(CH$_2$CH$_2$CH(CH$_3$)─ | 2-fluoroethyl | |
| 11 | nitro | —CH$_2$CH$_2$— | 2-chloroethyl | m.p. 138–140° C. |
| 12 | cyano | —(CH$_2$)$_3$— | 2,2,2-trifluoroethyl | |
| 13 | nitro | —CH$_2$CH$_2$— | 2,2,2-trichloroethyl | |
| 14 | nitro | —CH$_2$CH$_2$— | 2,2,2-tribromoethyl | |
| 15 | cyano | —CH$_2$CH$_2$— | 2,2,3,3-tetrafluoroethyl | |
| 16 | nitro | —CH$_2$CH$_2$— | 4-chlorobutyl | |
| 17 | cyano | —CH$_2$CH$_2$— | 2-methoxyethyl | |
| 18 | nitro | —CH$_2$CH$_2$— | 2-isopropoxyethyl | |
| 19 | nitro | —(CH$_2$)$_3$— | 2-(2-methoxyethoxy)ethyl | |
| 20 | nitro | —CH$_2$CH$_2$— | 4-chloro-phenoxymethyl | |
| 21 | nitro | —CH$_2$CH(CH$_3$)CH$_2$— | 4-nitro-phenoxymethyl | |
| 22 | nitro | —CH$_2$CH$_2$— | 2-(2,6-dichlorophenoxy)-ethyl | m.p. 177–179° C. |
| 23 | nitro | —CH$_2$CH$_2$— | 2-(2,6-dichloro-4-trifluoro-methoxyphenoxy)-ethyl | m.p. 160–162° C. |
| 24 | nitro | —CH$_2$CH$_2$— | 2-(4-chlorophenoxy)-ethyl | m.p. 95–96° C. |
| 25 | nitro | —CH$_2$CH$_2$— | 2-(3-chlorophenoxy)-ethyl | m.p. 108–110° C. |
| 26 | nitro | —CH$_2$CH$_2$— | 2-(2-chlorophenoxy)-ethyl | m.p. 153–156° C. |
| 27 | nitro | —CH$_2$CH$_2$— | 2-phenoxyethyl | m.p. 93–95° C. |
| 28 | cyano | —(CH$_2$)$_3$— | 2-p-tolyloxyethyl | |
| 29 | cyano | —CH$_2$C(CH$_3$)$_2$— | 2-(2,4-dichloro-phenoxy)-ethyl | |
| 30 | nitro | —CH$_2$CH$_2$— | 2-(3-trifluoromethyl-phenoxy)-ethyl | m.p. 125–128° C. |
| 31 | nitro | —CH$_2$CH$_2$— | 3-(3-trifluoromethyl-phenoxy)-propyl | m.p. 75–79° C. |

TABLE 1-continued

| Compound | Y | A | Z | Physical constant |
|---|---|---|---|---|
| 32 | cyano | —CH₂CH₂— | 2-(benzyloxy)-ethyl | |
| 33 | nitro | —CH₂CH₂— | 2-(5-chloro-2-pyridyloxy)-ethyl | m.p. 189–191° C. |
| 34 | nitro | —CH₂CH₂— | 2-(3,5-dichloro-2-pyridyloxy)-ethyl | m.p. 191–192° C. |
| 35 | cyano | —(CH₂)₃— | ethylthioethyl | |
| 36 | nitro | —CH₂CH₂— | 2-ethylthioethyl | |
| 37 | nitro | —CH₂CH₂— | 2-ethylsulfinylethyl | |
| 38 | nitro | —CH₂CH₂— | 2-ethylsulfonylethyl | |
| 39 | cyano | —CH₂CH₂— | 2-isopropylthioethyl | |
| 40 | nitro | —CH₂CH₂— | 3-methylthio-propyl | m.p. 93–95° C. |
| 41 | nitro | —CH₂CH₂— | 4-chloro-phenylthiomethyl | |
| 42 | cyano | —CH₂CH₂— | 2-(2-chlorophenylthio)-ethyl | |
| 43 | cyano | —CH₂CH₂— | 2-(4-nitro-phenylthio)-ethyl | |
| 44 | nitro | —(CH₂)₃— | 2-(2-chloro-6-pyridylthio)-ethyl | |
| 45 | nitro | —CH₂CH₂— | 2-(2-thiazolylthio)-ethyl | |
| 46 | nitro | —CH₂CH₂— | 2-thiocyanato-ethyl | |
| 47 | nitro | —CH₂CH₂— | thiocyanato-methyl | m.p. 261–265° C. |
| 48 | cyano | —(CH₂)₃— | 2-dimethylamino-ethyl | |
| 49 | nitro | —CH₂CH₂— | 2-N—methyl-N—butylamino-ethyl | |
| 50 | nitro | —CH₂CH₂— | 2-(4-chloro-2-methylanilino)-ethyl | |
| 51 | nitro | —CH₂CH₂— | 2-(N—methylanilino)-ethyl | |
| 52 | nitro | —CH₂CH₂— | 2-(N—methyl-N—2-chloro-6-pyridylamino)-ethyl | |
| 53 | nitro | —(CH₂)₃— | cyanomethyl | |
| 54 | nitro | —CH₂CH₂— | 1-cyanoethyl | |
| 55 | nitro | —CH₂CH₂— | 2-cyanoethyl | m.p. 136–139° C. |
| 56 | cyano | —CH₂CH₂— | 3-cyanopropyl | |
| 57 | nitro | —CH₂CH₂— | acetylmethyl | |
| 58 | nitro | —CH₂CH₂— | 3,3-dimethyl-2-butanon-1-yl | m.p. 158–159° C. |
| 59 | cyano | —CH₂CH₂— | 3,3-dimethyl-2-butanon-1-yl | m.p. 141–145° C. |
| 60 | nitro | —CH₂CHCH₂— (Cl substituent) | benzoylmethyl | |
| 61 | nitro | —CH₂CH₂— | 4-chlorobenzoyl-methyl | |
| 62 | nitro | —CH₂CH₂— | α-naphthoyl-methyl | |
| 63 | cyano | —(CH₂)₃— | trifluoroacetyl-methyl | |
| 64 | cyano | —CH₂CH₂— | 2-acetylethyl | |
| 65 | nitro | —CH₂CH₂— | 4-pyridylcarbonyl-methyl | m.p. 192–194° C. |
| 66 | nitro | —CH₂CH₂— | 3-pyridylcarbonyl-methyl | m.p. 176–177° C. |
| 67 | nitro | —CH₂CH₂— | 2-pyridylcarbonyl-methyl | m.p. 169–173° C. |
| 68 | cyano | —(CH₂)₃— | ethoxycarbonyl-methyl | |
| 69 | nitro | —CH₂CH₂— | 1-ethoxycarbonyl-ethyl | m.p. 66–69° C. |
| 70 | nitro | —CH₂CH₂— | phenoxycarbonylmethyl | |
| 71 | cyano | —(CH₂)₃— | 3-methylphenoxy-carbonylmethyl | |
| 72 | nitro | ɭCH₂CHɭ (CH₃ substituent) | benzyloxycarbonyl-methyl | |
| 73 | nitro | —CH₂CH₂— | 2-methoxycarbonyl-ethyl | |
| 74 | nitro | —CH₂CH₂— | carbamoylmethyl | |
| 75 | cyano | —(CH₂)₃— | isopropylaminocarbonyl-methyl | |
| 76 | nitro | —CH₂CH₂— | dimethylaminocarbonyl-methyl | |
| 77 | nitro | —(CH₂)₃— | 1-diethylamino-carbonyl-ethyl | |
| 78 | nitro | —CH₂CH₂— | anilinocarbonyl-methyl | |
| 79 | nitro | —CH₂CH₂— | N—methylanilocarbonyl-methyl | |
| 80 | nitro | —CH₂CH₂— | 2-diethylamino-carbonyl-ethyl | |
| 81 | nitro | —CH₂CH₂— | hydroxymethyl | |
| 82 | nitro | —(CH₂)₃— | hydroxymethyl | |
| 83 | nitro | —CH₂CH₂— | 2-hydroxy-ethyl | m.p. 128–130° C. |
| 84 | cyano | —CH₂CH₂— | 3-hydroxy-propyl | |
| 85 | nitro | —CH₂CH₂— | 1,3-dihydroxy-propyl | |
| 86 | nitro | —CH₂CH₂— | 2-acetyloxy-ethyl | |
| 87 | cyano | —CH₂CH₂— | 2-trifluoro-acetyloxy-ethyl | |
| 88 | nitro | —CH₂CH₂— | 2-benzoyloxy-ethyl | |
| 89 | nitro | —CH₂CH₂— | 2-methylsulfonyloxy-ethyl | |
| 90 | nitro | —CH₂CH₂— | 2-tosyloxy-ethyl | |
| 91 | nitro | —CH₂CH₂— | 2-dimethylamino-carbonyloxyethyl | |
| 92 | nitro | —CH₂CH₂— | 2,2,2-trichloro-1-hydroxyethyl | |
| 93 | nitro | —CH₂CH₂— | α-hydroxy-4-chloro-benzyl | |
| 94 | nitro | —CH₂CH₂— | 2-(O,O—diethyl-thiophosphono-thio)-ethyl | |
| 95 | nitro | —CH₂CH₂— | 2-(O—ethyl-S—propylthiophosphono-oxy)-ethyl | |
| 96 | nitro | —CH₂CH₂— | 2-(O,O—dimethylphosphono)-ethyl | |
| 97 | nitro | —CH₂CH₂— | trimethylsilyl-methyl | |
| 98 | cyano | —CH₂CH₂— | 2-trimethylsilyl-ethyl | |
| 99 | cyano | —CH₂CH₂— | trimethylsilylmethyl | |
| 100 | nitro | —(CH₂)₃— | 7-quinolyl-methyl | |
| 101 | nitro | —CH₂CH₂— | 2-chloro-isoquinolin-4-yl-methyl | m.p. 220–222° C. |
| 102 | nitro | —CH₂CH₂— | 2-methylthio-1,3-benzothiazol-5-yl-methyl | |
| 103 | cyano | —CH₂CH₂— | 6-quinoxalinyl | |
| 104 | nitro | —CH₂CH₂— | 2-chloro-1,3-benzothiazol-6-yl-methyl | m.p. 218–221° C. |

TABLE 1-continued

| Compound | Y | A | Z | Physical constant |
|---|---|---|---|---|
| 105 | cyano | —CH₂CH(CH₃)CH₂— | phenyl | |
| 106 | cyano | —CH₂CH₂— | 2,4-dichloro-phenyl | |
| 107 | nitro | —(CH₂)₃— | 4-nitrophenyl | |
| 108 | nitro | —CH₂CH₂— | 4-(4-trifluoromethyl-phenoxy)-phenyl | |
| 109 | nitro | —CH₂CH₂— | 3,5-dichloro-2-pyridyl | m.p. 151–155° C. |
| 110 | nitro | —CH₂CH₂— | 2-thiazolyl | m.p. 159–162° C. |
| 111 | cyano | —(CH₂)₃— | 1,3,4-thiadiazol-2-yl | |
| 112 | nitro | —CH₂CH₂— | 5-methyl-2-pyrimidinyl | |
| 113 | cyano | —(CH₂)₃— | 1,3-benzothiazol-2-yl | |
| 114 | nitro | —CH₂CH₂— | 1,3-benzoxazol-2-yl | m.p. >250° C. |
| 115 | nitro | —CH₂CH₂— | 6-fluoro-2-quinolyl | |
| 116 | nitro | —CH₂CH₂— | 6-chloro-2-quinoxalinyl | |
| 117 | cyano | —CH₂CH₂— | 4-pyridyl | |
| 118 | nitro | —CH₂CH₂— | 5-trifluoromethyl-2-pyridyl | m.p. 239–241° C. |
| 119 | nitro | —CH₂CH₂— | 4,5-dichloro-2-thiazolyl | |
| 120 | nitro | —CH₂CH₂— | allyl | m.p. 86–90° C. |
| 121 | nitro | —CH₂CH₂— | 4-pentenyl | |
| 122 | nitro | —CH₂CH₂— | 3-chloroallyl | m.p. 110–113° C. |
| 123 | nitro | —CH₂CH₂— | 4-chloro-2-butenyl | m.p. 224–227° C. |
| 124 | cyano | —CH₂C(CH₃)₂CH₂— | 2,3,3-trichloro-allyl | |
| 125 | nitro | —(CH₂)₃— | propargyl | |
| 126 | nitro | —CH₂CH₂— | 3-iodo-propargyl | |
| 127 | nitro | —CH₂CH₂— | methoxy | |
| 128 | nitro | —CH₂CH₂— | ethoxy | |
| 129 | cyano | —CH₂CH₂— | phenoxy | |
| 130 | nitro | —(CH₂)₃— | benzyloxy | |
| 131 | nitro | —CH₂CH₂— | allyloxy | |
| 132 | nitro | —CH₂CH₂— | 3-pyridylmethyloxy | |
| 133 | nitro | —(CH₂)₃— | methylthio | |
| 134 | nitro | —CH₂CH₂— | isopropylthio | |
| 135 | nitro | —CH₂CH₂— | trichloromethylthio | |
| 136 | nitro | —CH₂CH₂— | chloro-difluoromethyl-thio | |
| 137 | cyano | —CH₂CH₂— | 4-chloro-phenylthio | |
| 138 | nitro | —CH₂CH₂— | p-tolylthio | |
| 139 | nitro | —CH₂CH₂— | 4-chloro-benzylthio | |
| 140 | nitro | —CH₂CH₂— | dimethylamino | |
| 141 | nitro | —(CH₂)₃— | diethylamino | |
| 142 | cyano | —CH₂CH₂— | ethyl-carbonyl | m.p. 208–210° C. |
| 143 | cyano | ɬCH₂CH(CH₃)— | isopropyl-carbonyl | |
| 144 | nitro | —CH₂CH₂— | n-propylcarbonyl | m.p. 126–130° C. |
| 145 | nitro | —CH₂CH₂— | n-butylcarbonyl | |
| 146 | nitro | —CH₂CH₂— | n-octylcarbonyl | |
| 147 | cyano | —(CH₂)₃— | cyclopropylcarbonyl | |
| 148 | nitro | —CH₂CH₂— | 2,2-dichloro-3,3-dimethyl-cyclopropyl-carbonyl | |
| 149 | nitro | —CH₂CH₂— | cyclohexyl-carbonyl | |
| 150 | nitro | —(CH₂)₃— | 4-methyl-cyclohexyl-carbonyl | |
| 151 | nitro | —CH₂CH₂— | bromoacetyl | mp. 136–140° C. (decomp.) |
| 152 | cyano | —CH₂CH₂— | trifluoro-acetyl | |
| 153 | nitro | —(CH₂)₃— | trichloro-acetyl | |
| 154 | nitro | —CH₂CH₂— | dichloroacetyl | |
| 155 | nitro | —CH₂CH₂— | 1,1-dichloroethyl-carbonyl | |
| 156 | nitro | —CH₂CH₂— | methoxyacetyl | |
| 157 | nitro | —CH₂CH₂— | 1-(4-chlorophenoxy)-ethyl-carbonyl | |
| 158 | nitro | —CH₂CH₂— | methylthioacetyl | |
| 159 | nitro | —CH₂CH₂— | acetyloxy-acetyl | |
| 160 | nitro | —(CH₂)₃— | acryloyl | |
| 161 | cyano | —(CH₂)₃— | 1-propenyl-carbonyl | |
| 162 | cyano | —CH₂CH₂— | trichloro-acryloyl | |
| 163 | nitro | —CH₂CH₂— | propargyl-carbonyl | |
| 164 | nitro | —CH₂CH₂— | benzylcarbonyl | |
| 165 | nitro | —CH₂CH₂— | cyanoacetyl | |
| 166 | nitro | —CH₂CH₂— | 1-cyano-ethylcarbonyl | |
| 167 | nitro | —CH₂CH₂— | acetyl-acetyl | |
| 168 | cyano | —CH₂CH₂— | 5-quinolyl-carbonyl | |
| 169 | nitro | —CH₂CH₂— | 3,7-dichloro-5-quinolylcarbonyl | |
| 170 | nitro | —CH₂CH₂— | 6-quinoxalyl-carbonyl | |

TABLE 1-continued

| Compound | Y | A | Z | Physical constant |
|---|---|---|---|---|
| 171 | nitro | —CH(CH₃)—CH(CH₃)— | cyclopentyloxy-carbonyl | |
| 172 | cyano | —(CH₂)₃— | 2-methyl-cyclohexyloxy-carbonyl | |
| 173 | nitro | —CH₂CH₂— | 2-methoxy-ethoxy-carbonyl | |
| 174 | nitro | —CH₂CH₂— | 2-(3,4-dichloro-phenoxy)-ethoxy-carbonyl | |
| 175 | nitro | —CH₂CH₂— | 2-diethylamino-ethoxy-carbonyl | |
| 176 | nitro | —(CH₂)₂— | 2-ethylthio-ethoxy-carbonyl | |
| 177 | cyano | —CH₂CH₂— | 2-chloro-ethoxy-carbonyl | |
| 178 | nitro | —CH₂CH₂— | 2,2,2-trifluoro-ethoxy-carbonyl | |
| 179 | nitro | —CH₂CH₂— | 3-bromo-propoxy-carbonyl | |
| 180 | nitro | —CH₂CH₂— | 2,2,3,3-tetrafluoro-propoxy-carbonyl | |
| 181 | nitro | —CH₂CH₂— | 2-hydroxy-ethoxycarbonyl | |
| 182 | nitro | —CH₂CH₂— | allyloxy-carbonyl | |
| 183 | nitro | —CH₂CH₂— | 3-chloro-allyloxy-carbonyl | |
| 184 | nitro | —(CH₂)₃— | 2,3,3-trichloro-allyloxy-carbonyl | |
| 185 | nitro | —CH₂CH₂— | propargyloxy-carbonyl | |
| 186 | cyano | —CH₂CH₂— | 3-iodo-propargyloxy-carbonyl | |
| 187 | nitro | —CH₂CH₂— | 2-chloro-phenoxy-carbonyl | |
| 188 | nitro | —CH₂CH₂— | 4-nitro-m-tolyloxy-carbonyl | |
| 189 | nitro | —CH₂CH₂— | 4-chloro-o-tolyloxy-carbonyl | |
| 190 | nitro | —(CH₂)₃— | 4-trifluoromethyl-phenoxy-carbonyl | |
| 191 | nitro | —CH₂CH₂— | 3-dimethylamino-phenoxy-carbonyl | |
| 192 | nitro | —CH₂CH₂— | 4-bromo-2-chloro-phenoxy-carbonyl | |
| 193 | cyano | —CH₂CH₂— | 2,5-dichloro-4-iodo-phenoxy-carbonyl | |
| 194 | nitro | —CH₂CH₂— | 4-methylthio-m-tolyloxy-carbonyl | |
| 195 | nitro | —CH₂CH₂— | 4-methylsulfinyl-phenoxy-carbonyl | |
| 196 | nitro | —CH₂CH₂— | 4-cyanophenoxy-carbonyl | |
| 197 | nitro | —CH₂CH₂— | 2-isopropoxycarbonyl-phenoxy-carbonyl | |
| 198 | nitro | —CH₂CH₂— | 2-sec-butyl-phenoyx-carbonyl | |
| 199 | nitro | —(CH₂)₃— | 2-isopropoxy-phenoxy-carbonyl | |
| 200 | nitro | —CH₂CH₂— | 4-(5-trifluoromethyl-2-pyridyloxy)-phenoxy-carbonyl | |
| 201 | cyano | —CH₂CH₂— | ethylthio-carbonyl | |
| 202 | cyano | —CH₂CH₂— | phenylthio-carbonyl | |
| 203 | nitro | —CH₂CH₂— | benzyloxy-carbonyl | m.p. 179–182° C. |
| 204 | nitro | —CH₂CH₂— | 2,4-dichloro-benzyloxy-carbonyl | |
| 205 | nitro | —CH₂CH(CH₃)CH₂— | 3-trifluoromethyl-benzyloxy-carbonyl | |
| 206 | nitro | —CH₂CH₂— | 4-methoxybenzyloxy-carbonyl | |
| 207 | nitro | —CH₂CH₂— | 3-phenoxybenzyloxy-carbonyl | |
| 208 | nitro | —CH₂CH₂— | α-methylbenzyloxy-carbonyl | |
| 209 | nitro | —CH₂CH₂— | 3-pyridyloxy-carbonyl | |
| 210 | nitro | —CH₂CH₂— | 3,5,6-trichloro-2-pyridyloxy-carbonyl | |
| 211 | nitro | —CH₂CH₂— | 3-thienyloxy-carbonyl | |
| 212 | nitro | —CH₂CH₂— | 3-methyl-5-pyrazolyloxy-carbonyl | |
| 213 | nitro | —CH₂CH₂— | 5-phenyl-3-iso-oxazolyloxy-carbonyl | |
| 214 | nitro | —CH₂CH₂— | 3-methyl-1-isopropyl-5-pyrazolyloxy-carbonyl | |
| 215 | nitro | —CH₂CH₂— | 5-chloro-1-isopropyl-1,2,4-traizol-3-yl-oxy-carbonyl | |
| 216 | nitro | —CH₂CH₂— | 2-pyrazyloxy-carbonyl | |
| 217 | nitro | —CH₂CH₂— | 2-isopropyl-6-methyl-4-pyrimidinyloxy-carbonyl | |
| 218 | nitro | —CH₂CH₂— | 1H—6-oxo-3-pyridazinyloxy-carbonyl | |
| 219 | nitro | —CH₂CH₂— | 1-phenyl-6-oxo-3-pyridazinyloxy-carbonyl | |
| 220 | nitro | —CH₂CH₂— | 2-quinoxalinyloxy-carbonyl | |
| 221 | nitro | —CH₂CH₂— | 1-benzothiophen-4-yl-oxy-carbonyl | |
| 222 | nitro | —CH₂CH₂— | 2,2-dimethyl-dihydro-benzofuran-7-yl-oxy-carbonyl | |
| 223 | nitro | —CH₂CH₂— | 3-chloro-4-methyol-2-oxo-2H—1-benzopyran-7-yl-oxy-carbonyl | |
| 224 | cyano | —CH₂CH₂— | carbamoyl | |
| 225 | nitro | —CH₂CH₂— | ethylamino-carbonyl | m.p. 145–148° C. |
| 226 | nitro | —CH₂CH₂— | isopropylamino-carbonyl | m.p. 148–150° C. |
| 227 | nitro | —(CH₂)₃— | cyclohexylamino-carbonyl | |
| 228 | cyano | —CH₂CH₂— | anilino-carbonyl | |
| 229 | nitro | —CH₂CH₂— | 3-chloro-4-fluoro-anilino-carbonyl | |
| 230 | nitro | —CH₂C(CH₃)(CH₃)CH₂— | 2,6-diethylanilino-carbonyl | |
| 231 | nitro | —CH₂CH₂— | 2,4-dichloro-5-isopropoxy-anilino-carbonyl | |
| 232 | nitro | —CH₂CH₂— | dimethylamino-carbonyl | m.p. 147–148° C. |
| 233 | nitro | —(CH₂)₃— | diethylamino-carbonyl | |
| 234 | nitro | —CH₂CH₂— | diisobutylamino-carbonyl | |
| 235 | nitro | —(CH₂)₃— | pyrrolidino-carbonyl | |
| 236 | cyano | —CH₂CH₂— | 2-piperidino-carbonyl | |
| 237 | cyano | —CH₂CH₂— | 2,6-dimethyl-morpholino-carbonyl | |

TABLE 1-continued

| Compound | Y | A | Z | Physical constant |
|---|---|---|---|---|
| 238 | nitro | —CH₂CH₂— | N—methyl-m-toluidino-carbonyl | |
| 239 | nitro | —CH₂CH₂— | N—isopropylanilino-carbonyl | |
| 240 | nitro | —CH₂CH₂— | N—methyl-2,6-diethyl-anilino-carbonyl | |
| 241 | nitro | —CH₂CH₂— | N,N—diphenylamino-carbonyl | |
| 242 | nitro | —CH₂CH₂— | 3-pyridylamino-carbonyl | |
| 243 | nitro | —CH₂CH₂— | N—methyl-2-methoxy-6-pyridyl-amino-carbonyl | |
| 244 | nitro | —CH₂CH₂— | N—methyl-furylamino-carbonyl | |
| 245 | nitro | —CH₂CH₂— | N—methyl-iso-oxazolylamino-carbonyl | |
| 246 | nitro | —CH₂CH₂— | 5-tert-butyl-3-iso-oxazolylamino-carbonyl | |
| 247 | nitro | —CH₂CH₂— | 5-chloro-4-methyl-2-thiazolylamino-carbonyl | |
| 248 | nitro | —CH₂CH₂— | N—methyl-2-trifluoromethyl-1,3,4-thiadiazol-5-yl-amino-carbonyl | |
| 249 | nitro | —CH₂CH₂— | N—methyl-2-ethylsulfonyl-1,3,4-thiadiazol-5-yl-amino-carbonyl | |
| 250 | nitro | —(CH₂)₃— | 3-pyridylamino-carbonyl | |
| 251 | nitro | —CH₂CH₂— | 2-benzimidazolyl-amino-carbonyl | |
| 252 | nitro | —CH₂CH₂— | N—methyl-benzylamino-carbonyl | |
| 253 | nitro | —(CH₂)₃— | α,α-dimethyl-benzylamino-carbonyl | |
| 254 | nitro | —CH₂CH₂— | 2-picolylamino-carbonyl | |
| 255 | nitro | —CH₂CH₂— | N—methyl-2-furfurylamino-carbonyl | |
| 256 | nitro | —CH₂CH₂— | N—methyl-2-tetrahydrofurfurylamino-carbonyl | |
| 257 | nitro | —CH₂CH₂— | N—methyl-perhydrooxazin-2-yl-methyl-amino-carbonyl | |
| 258 | nitro | —CH₂CH₂— | allylamino-carbonyl | |
| 259 | nitro | —CH₂CH₂— | propargylamino-carbonyl | |
| 260 | cyano | —CH₂CH₂— | N,N—diallylamino-carbonyl | |
| 261 | nitro | —CH₂CH₂— | ethoxyalyl | |
| 262 | nitro | —CH₂CH₂— | 4-chloro-phenoxalyl | |
| 263 | nitro | —CH₂CH₂— | benzyl-oxalyl | |
| 264 | nitro | —CH₂CH₂— | methyl-sulfonyl | |
| 265 | nitro | —(CH₂)₃— | chloromethyl-sulfonyl | |
| 266 | cyano | —CH₂CH₂— | trifluoromethyl-sulfonyl | |
| 267 | nitro | —CH₂CH₂— | n-butyl-sulfonyl | |
| 268 | nitro | —CH₂CH₂— | 2-chloroethyl-sulfonyl | |
| 269 | nitro | —(CH₂)₃— | phenylsulfonyl | |
| 270 | nitro | —CH₂CH₂— | tosyl | |
| 271 | nitro | —CH₂CH₂— | 2-chlorophenyl-sulfonyl | |
| 272 | nitro | —CH₂CH₂— | 2-nitrophenyl-sulfonyl | |
| 273 | nitro | —CH₂CH₂— | 2-methyl-5-nitrophenyl-sulfonyl | m.p. 193–197° C. |
| 274 | cyano | —CH₂CH₂— | methoxy-sulfonyl | |
| 275 | nitro | —CH₂CH₂— | cyclohexyloxy-carbonyl | |
| 276 | nitro | ╒CH₂C(CH₃)(CH₃)╕ | phenoxy-sulfonyl | |
| 277 | nitro | —CH₂CH₂— | methylamino-sulfonyl | |
| 278 | nitro | —CH₂CH₂— | isopropylamino-sulfonyl | |
| 279 | nitro | —CH₂CH₂— | diethylamino-sulfonyl | |
| 280 | nitro | —CH₂CH₂— | anilino-sulfonyl | |
| 281 | nitro | —CH₂CH₂— | N—methylanilino-sulfonyl | |
| 282 | nitro | —CH₂CH₂— | O,O—dimethyl-phosphono | |
| 283 | nitro | —CH₂CH₂— | O—ethyl-O—isopropyl-phosphono | |
| 284 | nitro | —CH₂CH₂— | O—ethyl-S—propyl-thio-phosphono | |
| 285 | nitro | —CH₂CH₂— | O,O—diethylthio-phosphono | |
| 286 | nitro | —CH₂CH₂— | O—ethyl-O—2,4-dichlorophenylthio-phosphono | |
| 287 | nitro | —CH₂CH₂— | O—ethyl-N—isopropylamido-thio-phosphono | |
| 288 | nitro | —CH₂CH₂— | 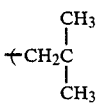 | |
| 289 | nitro | —CH₂CH₂— | 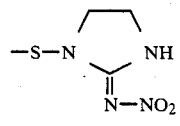 | |
| 290 | nitro | —CH₂CH₂— | 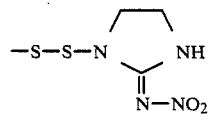 | |

TABLE 1-continued

| Compound | Y | A | Z | Physical constant |
|---|---|---|---|---|
| 291 | nitro | —CH$_2$CH$_2$— | ![structure: -C(=O)-C(=O)-N<(CH$_2$CH$_2$)>NH with N=NO$_2$ (nitroimidazolidine)] | |
| 292 | nitro | —CH$_2$CH$_2$— | ![structure: -C(=S)-N<(CH$_2$CH$_2$)>NH with N=NO$_2$] | |
| 293 | nitro | —CH$_2$CH$_2$— | ![structure: -S(=O)$_2$-N<(CH$_2$CH$_2$)>NH with N=NO$_2$] | |
| 294 | nitro | —CH$_2$CH$_2$— | —CH$_2$—N<(CH$_2$CH$_2$)>NH with N=NO$_2$ | |
| 295 | nitro | —CH$_2$CH$_2$— | —(CH$_2$)$_2$—N<(CH$_2$CH$_2$)>NH with N=NO$_2$ | |
| 296 | nitro | —CH$_2$CH$_2$— | CH$_3$—CH—N<(CH$_2$CH$_2$)>NH with N=NO$_2$ | |
| 297 | nitro | —CH$_2$CH$_2$— | n-butyl | mp. 65–68° C. |
| 298 | nitro | —CH$_2$CH$_2$— | tert-butyl | |
| 299 | cyano | —CH$_2$CH$_2$— | n-octyl | |
| 300 | nitro | —CH$_2$CH$_2$— | 4-methyl-benzyl | |
| 301 | nitro | —CH$_2$CH$_2$— | 4-chloro-benzyl | |
| 302 | cyano | —CH$_2$CH$_2$— | 2-bromo-benzyl | |
| 303 | nitro | —(CH$_2$)$_3$— | 2,4-dichloro-benzyl | |
| 304 | nitro | —CH$_2$CH$_2$— | 4-nitro-benzyl | |
| 305 | nitro | —CH$_2$CH$_2$— | 4-methoxy-benzyl | |
| 306 | nitro | —CH$_2$CH$_2$— | 3-trifluoromethyl-benzyl | |
| 307 | nitro | —CH$_2$CH$_2$— | 3,4-methylenedioxy-benzyl | |
| 308 | nitro | —CH$_2$CH$_2$— | α-methylbenzyl | |
| 309 | nitro | —CH$_2$CH$_2$— | 4-bromobenzyl | |
| 310 | cyano | —CH$_2$CH$_2$— | 2-furfuryl | |
| 311 | nitro | —CH$_2$CH$_2$— | 5-methyl-2-furfuryl | |
| 312 | nitro | ✦CH$_2$CH(CH$_3$)— | 2-thienyl | |
| 313 | nitro | —CH$_2$CH$_2$— | 5-bromo-2-thienyl | |
| 314 | nitro | —CH$_2$CH$_2$— | 1-methyl-2-pyrrolyl-methyl | |
| 315 | nitro | —CH$_2$CH$_2$— | 3-phenyl-5-iso-oxazolyl-methyl | |
| 316 | nitro | —CH$_2$CH$_2$— | 5-imidazolyl-methyl | |
| 317 | nitro | —CH$_2$CH$_2$— | 5-isothiazolyl-methyl | |
| 318 | nitro | —CH$_2$CH$_2$— | 4-methyl-thiazolyl-methyl | |
| 319 | nitro | —CH$_2$CH$_2$— | 2-trifluoromethyl-1,3,4-oxadiazol-5-yl-methyl | |
| 320 | nitro | —CH$_2$CH$_2$— | 1,3,4-thiadiazol-2-yl-methyl | |
| 321 | nitro | —CH$_2$CH$_2$— | 1,2,3,4-tetrazol-5-yl-methyl | |
| 322 | nitro | —CH$_2$CH$_2$— | 2-pyrimiinyl-methyl | |
| 323 | nitro | —CH$_2$CH$_2$— | 6-chloro-4-pyrazinyl-methyl | |
| 324 | nitro | —CH$_2$CH$_2$— | 4,6-dichloro-1,3,5-triazin-2-yl-methyl | |
| 325 | cyano | —CH$_2$CH$_2$— | 2-(2-furyl)-ethyl | |
| 326 | nitro | —CH$_2$CH$_2$— | 2-(2-chloro-6-pyridyl)-ethyl | mp. 170–173° C. |
| 327 | nitro | —CH$_2$CH$_2$— | 3-(2-chloro-5-pyridyl)-propyl | mp. 116–118.5° C. |
| 328 | nitro | —CH$_2$CH$_2$— | 2-tetrahydro-furfuryl | |
| 329 | nitro | —CH$_2$CH$_2$— | 3-tetrahydrothienyl-methyl | |
| 330 | nitro | —CH$_2$CH$_2$— | 1-methyl-2-pyrrolidinyl-methyl | |
| 331 | nitro | —CH$_2$CH$_2$— | 4,5-dihydro-iso-oxazol-5-yl-methyl | |

4,880,933

TABLE 1-continued

| Compound | Y | A | Z | Physical constant |
|---|---|---|---|---|
| 332 | nitro | —CH$_2$CH$_2$— | 3-methyl-5-tetrahydro-thiazolyl-methyl | |
| 333 | nitro | —CH$_2$CH$_2$— | 5-oxo-2-tetrahydro-furfuryl | |
| 334 | nitro | —CH$_2$CH$_2$— | 3-methyl-2-oxo-5-tetrahydro-thiazolyl-methyl | |
| 335 | nitro | —CH$_2$CH$_2$— | 2-oxo-1,3-dioxolan-4-yl-methyl | |
| 336 | nitro | —CH$_2$CH$_2$— | 1,3-dioxolan-2-yl-methyl | |
| 337 | nitro | —CH$_2$CH$_2$— | 1,3-oxathiolan-2-yl-methyl | |
| 338 | nitro | —CH$_2$CH$_2$— | 3-tetrahydro-pyranyl-methyl | |
| 339 | nitro | —CH$_2$CH$_2$— | 3-tetrahydro-thio-pyranyl-methyl | |
| 340 | nitro | —CH$_2$CH$_2$— | 2-oxo-1,3-oxathian-5-yl-methyl | |
| 341 | nitro | —CH$_2$CH$_2$— | 3-methyl-1,4-oxazin-2-yl-methyl | |
| 342 | nitro | —CH$_2$CH$_2$— | 1-ethyl-4-piperazinyl-methyl | |
| 343 | nitro | —CH$_2$CH$_2$— | 1-methyl-2-oxo-4-piperazinyl | |
| 344 | nitro | —(CH$_2$)$_3$— | methoxy-carbonyl | |
| 345 | nitro | —CH$_2$CH$_2$— | isopropoxy-carbonyl | |
| 346 | nitro | —(CH$_2$)$_3$— | hexyloxy-carbonyl | |
| 347 | nitro | —CH$_2$CH$_2$— | 2,4-dichloro-benzoyl | mp. 184–186° C. |
| 348 | cyano | —CH$_2$CH$_2$— | 3,5-dichloro-benzoyl | mp. 231–232° C. |
| 349 | nitro | —CH$_2$CH$_2$— | 2-methyl-benzoyl | |
| 350 | cyano | —CH$_2$CH$_2$— | 4-trifluoromethyl-benzoyl | |
| 351 | nitro | —(CH$_2$)$_3$— | 3,4-dimethoxy-benzoyl | |
| 352 | nitro | —CH$_2$CH$_2$— | 4-nitro-benzoyl | |
| 353 | nitro | —CH$_2$CH$_2$— | 2-acetylamino-benzoyl | |
| 354 | nitro | —CH$_2$CH$_2$— | α-naphthoyl | |
| 355 | cyano | —CH$_2$CH$_2$— | 2,5-dichloro-benzoyl | |
| 356 | nitro | —CH$_2$CH$_2$— | 4-ethoxy-methoxy-benzoyl | |
| 357 | nitro | —(CH$_2$)$_3$— | 2-pyridyl-carbonyl | |
| 358 | nitro | —CH$_2$CH$_2$— | 2-chloro-5-pyridyl-carbonyl | |
| 359 | cyano | —(CH$_2$)$_3$— | 4-pyridyl-carbonyl | |
| 360 | nitro | —CH$_2$CH$_2$— | 2,6-dichloro-4-pyridyl-carbonyl | |
| 361 | nitro | —CH$_2$CH$_2$— | 2-furyl-carbonyl | mp. 160–162° C. |
| 362 | nitro | —CH$_2$CH$_2$— | 5-nitro-2-furyl-carbonyl | |
| 363 | nitro | —CH$_2$CH$_2$— | 2,5-dimethyl-3-furyl-carbonyl | |
| 364 | nitro | —CH$_2$CH$_2$— | 3-thienyl-carbonyl | |
| 365 | nitro | —CH$_2$CH$_2$— | 3,5-dichloro-2-thienyl-carbonyl | |
| 366 | nitro | —CH$_2$CH$_2$— | 1-methyl-4-pyrazolyl-carbonyl | |
| 367 | nitro | —CH$_2$CH$_2$— | 3-trifluoromethyl-5-iso-oxazolyl-carbonyl | |
| 368 | nitro | —CH$_2$CH$_2$— | 2-oxazolyl-carbonyl | |
| 369 | cyano | —CH$_2$CH$_2$— | 2-thiazolyl-carbonyl | |
| 370 | nitro | —CH$_2$CH$_2$— | 2-chloro-5-thiazolyl-carbonyl | |
| 371 | nitro | —(CH$_2$)$_3$— | 2,4-dichloro-5-thiazolyl-carbonyl | |
| 372 | nitro | —CH$_2$CH$_2$— | 5-isothiazolyl-carbonyl | |
| 373 | nitro | —CH$_2$CH$_2$— | 2-tert-butyl-1,3,4-oxadiazol-5-yl-carbonyl | |
| 374 | nitro | —CH$_2$CH$_2$— | 2-phenyl-1,3,4-thiadiazol-5-yl-carbonyl | |
| 375 | nitro | —CH$_2$CH$_2$— | 1,2,3-thiadiazol-5-yl-carbonyl | |
| 376 | nitro | —CH$_2$CH$_2$— | 5-tert-butyl-2-pyrimidinyl-carbonyl | |
| 377 | nitro | —CH$_2$CH$_2$— | 5-methyl-2-pyrazinyl-carbonyl | |
| 378 | nitro | —CH$_2$CH$_2$— | 4-pyridazinyl-carbonyl | |
| 379 | nitro | —CH$_2$CH$_2$— | 4,6-dichloro-1,3,5-triazin-2-yl-carbonyl | |
| 380 | nitro | —CH$_2$CH$_2$— | 4,6-dimethylthio-1,3,5-triazin-2-yl-carbonyl | |
| 381 | nitro | —CH$_2$CH$_2$— | 2-tetrahydro-furyl-carbonyl | |
| 382 | cyano | —CH$_2$CH$_2$— | 2-tetrahydro-thienyl-carbonyl | |
| 383 | nitro | —CH$_2$CH$_2$— | 2-methyl-3-oxo-5-tetrahydro-iso-oxazolyl-carbonyl | |
| 384 | nitro | —(CH$_2$)$_3$— | 1-methyl-3-pyrrolidinyl-carbonyl | |
| 385 | cyano | —CH$_2$CH$_2$— | 2-oxo-5-tetrahydro-thiazolyl-carbonyl | |
| 386 | nitro | —CH$_2$CH$_2$— | 3-methyl-5-tetrahydro-thiazolyl-carbonyl | |
| 387 | nitro | —CH$_2$CH$_2$— | 1-phenyl-4-piperazinyl-carbonyl | |
| 388 | nitro | —CH$_2$CH$_2$— | 3-methyl-1,4-oxazin-2-yl-carbonyl | |
| 389 | nitro | —CH$_2$CH$_2$— | phenethyl | |
| 390 | nitro | —CH$_2$CH$_2$— | dimethylamino-thio-carbonyl | |
| 391 | cyano | —(CH$_2$)$_3$— | 1-piperidino-thio-carbonyl | |
| 392 | nitro | —CH$_2$CH$_2$— | N—methyl-N—(2-methoxypyridin-6-yl)-amino-thio-carbonyl | |
| 393 | nitro | —(CH$_2$)$_3$— | 3-chloroallyl | $n_D$ 1.5985 |
| 394 | nitro | —CH$_2$CH$_2$— | O—ethyl-S—sec-butyl-thio-phosphono | $n_D$ 1.5550 |
| 395 | nitro | —CH$_2$CH$_2$— | 2-pyrimidinyl | mp. 185–188° C. |
| 396 | nitro | —CH$_2$CH$_2$— | pyrazinyl | mp. 179–182° C. |
| 397 | nitro | —CH$_2$CH$_2$— | 6-chloro-3-pyridazinyl | mp. 242–246° C. (decomp.) |
| 398 | nitro | —CH$_2$CH$_2$— | 6-chloro-4-pyrimidinyl | mp. 250–251° C. |
| 399 | nitro | —CH$_2$CH$_2$— | 4,6-dimethoxy-1,3,5-triazin-2-yl | mp. 210–212° C. (decomp.) |
| 400 | nitro | —CH$_2$CH$_2$— | 2-(2-pyridyl)-ethyl | mp. 105–109° C. |
| 401 | nitro | —CH$_2$CH$_2$— | 2,2-dimethoxy-ethyl | |
| 402 | cyano | —CH$_2$CH$_2$— | 2,2-dimethoxy-ethyl | |
| 403 | nitro | —CH$_2$CH$_2$— | cyano | mp. 176–180° C. (decomp.) |
| 404 | cyano | —CH$_2$CH$_2$— | cyano | mp. >300° C. |
| 405 | nitro | —CH$_2$CH$_2$— | 2-chloro-2-cyanoethyl | $n_D^{20}$ 1.5776 |
| 406 | nitro | —CH$_2$CH$_2$— | 2-chloro-2-cyanovinyl | mp. 128–131° C. |
| 407 | nitro | —CH$_2$CH$_2$— | 3-cyanobenzyl | mp. 169–172° C. |
| 408 | nitro | —CH$_2$CH$_2$— | 2-cyanobenzyl | mp. 203–205° C. |
| 409 | nitro | —CH$_2$CH$_2$— | 4-cyanobenzyl | mp. 148–150° C. |

TABLE 1-continued

| Compound | Y | A | Z | Physical constant |
|---|---|---|---|---|
| 410 | nitro | —CH$_2$CH$_2$— | 3-cyano-4-fluoro-benzyl | mp. 159–161° C. |
| 411 | cyano | —CH$_2$CH$_2$— | 3-cyanobenzyl | mp. 146–150° C. |
| 412 | nitro | —(CH$_2$)$_3$— | 3-cyanobenzyl | mp. 140–142° C. |
| 413 | nitro | —CH$_2$CH$_2$— | phenyl | mp. 150–153° C. |
| 414 | nitro | —CH$_2$CH$_2$— | 4-(2,2,2-trifluoro-ethylthio)benzyl | mp. 85–88° C. |
| 415 | nitro | —CH$_2$CH$_2$— | 3-(2,2,2-trifluoro-ethoxy)benzyl | mp. 95–99° C. |
| 416 | nitro | —CH$_2$CH$_2$— | 6-chloronicotinoylmethyl | mp. 221–225° C. |
| 417 | nitro | —CH$_2$CH$_2$— | 4-(1,1,2,3,3,3-hexafluoro propoxy)benzyl | n$_D^{40}$ 1.5010 |
| 418 | nitro | —CH$_2$CH$_2$— | propargyl | mp. 156–160° C. |
| 419 | nitro | —Ch$_2$CH$_2$— | n-butylaminocarbonyl | mp. 103–107° C. |
| 420 | nitro | —CH$_2$CH$_2$— | anilinocarbonyl | mp. 192–195° C. |
| 421 | nitro | —CH$_2$CH$_2$— | 2-methoxyanilinocarbonyl | mp. 207–211° C. |
| 422 | nitro | —CH$_2$CH$_2$— | 4-chloro-3-cyanobenzyl | mp. 179–181° C. |

Referential example 1

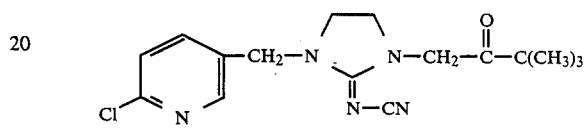

3.2 g of 1-[2-(3,5-dichloropyridyl-2-yl-oxy)ethyl]-2-nitroiminoimidazolidine were dissolved in 20 ml of dimethyl-formamide. To the resulting solution was added 0.4 g of 60% oil dispersed sodium hydride at room temperature. The reaction mixture thus obtained was stirred until the evolution of hydrogen had ceased. Next, 1.7 g of 2-chloro-5-chloromethylthiazole were added at room temperature, and the reaction mixture was stirred at room temperature for 1 hour, and then stirred at 40° C. for 30 minutes. After the completion of the reaction, the reaction mixture was poured into ice water, and extracted with dichloromethane. The extractant was treated so as to concentrate the dichloromethane. An amount of ether was added to the residue, so that the aimed product was deposited as crystals. The crystalline product was separated by filtration, washed in water and then dried. Yield: 2.7 g; mp. 77° to 80° C.

Referential example 2

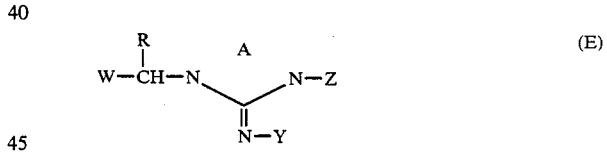

A mixture of 2.1 g of 1-(3,3-dimethyl-2-butanon-1-yl)-2-cyanoiminoimidazolidine, 1.6 g of 2-chloro-5-chloromethylpyridine, 1.4 g of anhydrous potassium carbonate and 30 ml of acetonitrile was refluxed under stirring for 8 hours. After the completion of the reaction, the acetonitrile was distilled off under a reduced pressure. The residue was admixed with dichloromethane and washed in water. After the dichloromethane had been concentrated, the reaction mixture was worked up by employing a silica gel column (wherein chloroform:ethanol=9:1), so that 0.9 g of the aimed product was obtained as a colorless viscous material. n$_D^{20}$=1.5446

By the same method as Examples 1 and 2 various compounds of the formula:

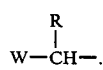 (E)

can be obtained, as shown in Table 2. In Table 2, the mark " " represents the bond of the nitrogen atom in the radical A connected to the bond of

R
|
W—CH—.

TABLE 2

| Compound | W | R | Y | A | Z | Physical constant |
|---|---|---|---|---|---|---|
| E-1 | 4-pyridyl | H | cyano | —CH₂CH₂— | methyl | mp. 107.5–108.5° C. |
| E-2 | 2-chloro-5-pyridyl | H | nitro | —CH₂CH₂— | methyl | |
| E-3 | 2-chloro-5-pyridyl | H | nitro | —CH₂CHCH₂— with Cl | methyl | |
| E-4 | 2-chloro-5-pyridyl | H | cyano | —CH₂CH₂— | methyl | mp. 101–103° C. |
| E-5 | 5-thiazolyl | H | cyano | —(CH₂)₃— | methyl | |
| E-6 | 5-chloro-2-pyridyl | H | nitro | —CH₂CH₂— | methyl | |
| E-7 | 1-methyl-4-imidazolyl | H | nitro | —CH₂CHCH₂— with OH | methyl | |
| E-8 | 2-methyl-4-pyrazinyl | H | nitro | —CH₂CH₂— | methyl | |
| E-9 | 2-methyl-5-oxazolyl | H | nitro | —CH₂CH₂— | ethyl | |
| E-10 | 2-chloro-1,3,4-thiadiazol-5-yl | H | nitro | —CH₂CH₂— | ethyl | mp. 138–142° C. |
| E-11 | 2-chloro-5-pyridyl | H | nitro | —CH₂CH₂— | isopropyl | |
| E-12 | 2-methyl-5-pyrimidinyl | H | nitro | —CH₂CH₂— | isopropyl | |
| E-13 | 4-pyridyl | methyl | nitro | —CH₂CH₂— | n-butyl | $n_D^{20}$ 1.5820 |
| E-14 | 2-chloro-5-pyridyl | H | nitro | —CH₂CH₂— | n-butyl | |
| E-15 | 4-isothiazolyl | H | nitro | —CH₂CH₂— | n-butyl | |
| E-16 | 3-methyl-5-isooxazolyl | H | nitro | —CH₂CH₂— | sec-butyl | |
| E-17 | 4-pyridazinyl | H | nitro | —(CH₂)₃— | sec-butyl | |
| E-18 | 2-chloro-5-pyridyl | H | nitro | —CH₂CH₂— | n-hexyl | |
| E-19 | 2-fluoro-5-thiazolyl | H | nitro | —CH₂CH₂— | difluoromethyl | |
| E-20 | 2-fluoro-5-thiazolyl | H | nitro | —(CH₂)₃— | difluoromethyl | |
| E-21 | 3-methyl-6-pyridazinyl | H | nitro | —CH₂CH₂— | trifluoromethyl | |
| E-22 | 2-fluoro-5-pyridyl | H | nitro | —(CH₂CH₂CH—) with CH₃ | 2-chloroethyl | |
| E-23 | 2-chloro-5-pyridyl | H | nitro | —CH₂CH₂— | 2-chloroethyl | |
| E-24 | 2-chloro-5-thiazolyl | H | nitro | —(CH₂)₃— | 2-chloroethyl | |
| E-25 | 2-fluoro-5-oxazolyl | H | nitro | —CH₂CH₂— | 2,2,2-trifluoroethyl | |
| E-26 | 2-bromo-5-pyridyl | H | cyano | —CH₂CH₂— | 3-chloropropyl | |
| E-27 | 3-pyridyl | H | nitro | —CH₂CH₂— | cyclohexylmethyl | |
| E-28 | 2-fluoro-5-pyridyl | H | nitro | —CH₂CH₂— | cyclopropylmethyl | |
| E-29 | 1,2,3-triadiazol-5-yl | H | nitro | —CH₂CH₂— | cyclopentyl | |
| E-30a | 2-chloro-5-pyridyl | methyl | nitro | —CH₂CH₂— | methoxymethyl | |
| E-30b | 2-chloro-5-pyridyl | H | cyano | —(CH₂CH₂CH—) with CH₃ | 2-(3-trifluoro-methylphenoxy)ethyl | mp. 82–85° C. |
| E-31a | 2-methyl-5-pyridyl | H | nitro | —CH₂CH₂— | 2-phenoxyethyl | |
| E-31b | 2-chloro-5-thiazolyl | H | nitro | —(CH₂)₃— | 2-(2,4-dichloro-5-pyridyloxy)ethyl | mp. 77–80° C. |
| E-32 | 2-trifluoromethyl-5-thiazolyl | H | nitro | —CH₂CH₂— | 4-chlorophenoxy-methyl | |
| E-33 | 3-chloro-6-pyridazinyl | H | cyano | —CH₂CH₂— | ethoxymethyl | |
| E-34 | 2-chloro-5-pyridyl | H | nitro | —CH₂CH₂— | 3-methylthiopropyl | $n_D^{20}$ 1.6067 |

4,880,933

TABLE 2-continued

| Compound | W | R | Y | A | Z | Physical constant |
|---|---|---|---|---|---|---|
| E-35 | 2-chloro-5-pyridyl | H | nitro | $\begin{array}{c}OCH_3\\|\\-CH_2CHCH_2-\end{array}$ | methylthiomethyl | |
| E-36 | 2-trifluoromethyl-5-thiazolyl | H | nitro | —(CH$_2$)$_3$— | isopropylthiomethyl | |
| E-37 | 2-chloro-5-pyridyl | H | nitro | —CH$_2$CH$_2$— | hydroxymethyl | |
| E-38 | 2-chloro-5-pyridyl | H | nitro | —CH$_2$CH$_2$— | 2-hydroxyethyl | |
| E-39 | 2-chloro-5-thiazolyl | H | cyano | —(CH$_2$)$_3$— | 3-hydroxypropyl | |
| E-40 | 2-chloro-5-pyridyl | H | nitro | —CH$_2$CH$_2$— | 2,2,2-trichloro-1-hydroxyethyl | |
| E-41 | 2-chloro-5-pyridyl | H | nitro | —CH$_2$CH$_2$— | 2-acetyloxyethyl | |
| E-42 | 2-bromo-5-pyridyl | H | nitro | —CH$_2$CH$_2$— | 2-(O,O—diethylthiophosphonothio)ethyl | |
| E-43 | 1,2,5-thiaziazol-3-yl | H | nitro | —CH$_2$CH$_2$— | thiocyanatomethyl | |
| E-44 | 2-chloro-5-pyridyl | H | nitro | —CH$_2$CH$_2$— | 2-thiocyanatoethyl | |
| E-45 | 2,4-dichloro-5-thiazolyl | H | nitro | —CH$_2$CH$_2$— | 2-thiocyanatoethyl | |
| E-46 | 5-oxazolyl | H | nitro | —CH$_2$CH$_2$— | 2-ethylsulfonylethyl | |
| E-47a | 2-difluoromethyl-5-pyridyl | H | nitro | —CH$_2$CH$_2$— | cyanomethyl | mp. 120–121° C. |
| E-47b | 2-chloro-5-pyridyl | H | nitro | —CH$_2$CH$_2$— | cyanomethyl | $n_D^{20}$ 1.6015 |
| E-48 | 2-chloro-5-pyridyl | H | cyano | —CH$_2$CH$_2$— | cyanomethyl | |
| E-49 | 3-methyl-5-isooxazolyl | H | nitro | —CH$_2$CH$_2$— | 1-cyanoethyl | |
| E-50 | 2-chloro-5-pyridyl | methyl | nitro | —CH$_2$CH$_2$— | 2-dimethylamino-ethyl | |
| E-51 | 2-fluoro-5-thiazolyl | H | nitro | —CH$_2$CH$_2$— | trimethylsilylethyl | |
| E-52 | 2-chloro-5-pyridyl | methyl | nitro | $\begin{array}{c}CH_3\\|\\\vdash CH_2C-\end{array}$ | benzyl | |
| E-53a | 2-chloro-5-pyridyl | H | cyano | —CH$_2$CH$_2$— | 4-chlorobenzyl | mp. 161–163° C. |
| E-53b | 2-fluoro-5-pyridyl | H | nitro | —CH$_2$CH$_2$— | 4-tert-butyl-benzyl | |
| E-54 | 2-trifluoromethyl-5-oxazolyl | H | nitro | —(CH$_2$)$_3$— | 3-trifluoromethyl-benzyl | |
| E-55 | 2-trifluoromethyl-5-pyridyl | H | nitro | —CH$_2$CH$_2$— | 4-chlorobenzoylmethyl | |
| E-56 | 2-chloro-5-pyridyl | H | nitro | —CH$_2$CH$_2$— | 1-(ethoxycarbonyl)-ethyl | $n_D^{20}$ 1.569 |
| E-57 | 2-chloro-5-pyridyl | H | cyano | —CH$_2$CH$_2$— | 1-(ethoxycarbonyl)-ethyl | |
| E-58 | 2-methyl-5-pyridyl | H | nitro | —CH$_2$CH$_2$— | m-tolyloxycarbonylmethyl | |
| E-59a | 2-difluoromethyl-5-thiazolyl | H | nitro | —(CH$_2$)$_3$— | 3,3-dimethyl-2-butanon-1-yl | mp. 105–110° C. |
| E-59b | 2-chloro-5-pyridyl | H | nitro | —CH$_2$CH$_2$ | 3,3-dimethyl-2-butanon-1-yl | |
| E-60 | 1-isopropyl-4-pyrazolyl | H | nitro | —CH$_2$CH$_2$— | 2-pyridylcarbonylmethyl | |
| E-61 | 2-trifluoromethylthio-5-pyridyl | H | nitro | —CH$_2$CH$_2$— | N—methylanilinocarbonylmethyl | |
| E-62 | 2-chloro-5-pyridyl | H | nitro | —CH$_2$CH$_2$— | 2-oxy-1,3-dioxan-4-yl | mp. 150–153° C. |
| E-63a | 4-isooxazolyl | H | cyano | —(CH$_2$)$_3$— | 2-oxolanylmethyl | |
| E-63b | 2-chloro-5-pyridyl | H | nitro | —CH$_2$CH$_2$— | 1-(dimethylaminocarbonyl)ethyl | |
| E-64 | 2-chloro-5-pyridyl | H | nitro | —CH$_2$CH$_2$— | 2-oxo-3-methyl-1,3-thiazolidin-5-yl-methyl | |
| E-65 | 2-fluoro-5-pyridyl | H | nitro | —CH$_2$CH$_2$— | 3-quinolinyl | |
| E-66 | 2-bromo-5-pyridyl | H | nitro | —CH$_2$CH$_2$— | 2-chloro-6-benzothiazolyl | |
| E-67 | 2-chloro-5-thiazolyl | H | nitro | —(CH$_2$)$_3$— | 5,6-dichloro-2-benzothiazolyl | |
| E-68a | 4-isothiazolyl | H | nitro | —CH$_2$CH$_2$— | phenethyl | |
| E-68b | 2-chloro-5-pyridyl | H | nitro | —CH$_2$CH$_2$— | 2-chloro-6-pyridyl | $n_D^{50}$ 1.6117 |
| E-69 | 3-trifluoromethyl-5-iso-oxazolyl | H | nitro | —(CH$_2$)$_3$— | 6-quinoxalinyl | |
| E-70 | 2-chloro-5-pyridyl | H | nitro | —CH$_2$CH$_2$— | phenyl | |
| E-71a | 2-chloro-5-thiazolyl | H | cyano | —CH$_2$CH$_2$— | 4-nitrophenyl | |

TABLE 2-continued

| Compound | W | R | Y | A | Z | Physical constant |
|---|---|---|---|---|---|---|
| E-71b | 2-chloro-5-pyridyl | H | nitro | —CH$_2$CH$_2$— | 3,5-dichloro-2-pyridyl | mp. 203–205° C. |
| E-72 | 2-chloro-5-pyrimidinyl | H | nitro | —CH$_2$CH$_2$— | 3,5-dichloro-2-pyridyl | |
| E-73 | 1-methyl-4-imidazolylmethyl | H | nitro | —(CH$_2$)$_3$— | 4,5-dichloro-2-thiazolyl | |
| E-74 | 4-pyridazinyl | methyl | nitro | —CH$_2$CH$_2$— | 2-benzoxazolyl | mp. 103–105° C. |
| E-75 | 2-chloro-5-pyridyl | H | nitro | —CH$_2$CH$_2$— | allyl | |
| E-76a | 3-chloro-5-oxazolyl | H | nitro | —CH$_2$CH$_2$— | 3-chloroallyl | $n_D^{20}$ 1.6095 |
| E-76b | 2-chloro-5-pyridyl | H | nitro | —CH$_2$CH$_2$— | 3-chloroallyl | |
| E-77a | 2,3-difluoro-5-pyridyl | H | nitro | —CH$_2$CH$_2$— | propargyl | $n_D^{20}$ 1.5667 |
| E-77b | 3-methyl-5-isooxazolyl | H | cyano | —(CH$_2$)$_3$— | propargyl | |
| E-78a | 2-chloro-5-pyridyl | H | cyano | —CH$_2$CH$_2$— | methoxy | |
| E-78b | 2-fluoro-5-thiazolyl | H | cyano | —CH$_2$CH$_2$— | 3-chloroallyl | |
| E-79 | 2-chloro-5-pyrazyl | H | nitro | —CH$_2$CH$_2$— | benzyloxy | |
| E-80 | 2-fluoro-5-pyridyl | H | nitro | —(CH$_2$)$_3$— | dichloro-fluoromethyl-thio | |
| E-81 | 2-chloro-5-pyridyl | H | nitro | —(CH$_2$)$_3$— | p-tolylthio | mp. 144.5–146° C. |
| E-82 | 2-bromo-5-pyridyl | H | nitro | —CH$_2$CH$_2$— | formyl | $n_D^{20}$ 1.5895 |
| E-83 | 2-chloro-5-pyridyl | H | nitro | —CH$_2$CH$_2$— | acetyl | mp. 53–55° C. |
| E-84 | 2-chloro-5-pyridyl | H | cyano | —CH$_2$CH$_2$— | acetyl | |
| E-85 | 2-chloro-5-pyridyl | H | nitro | —CH$_2$CH$_2$— | trifluoroacetyl | |
| E-86 | 2-chloro-5-pyridyl | H | cyano | —CH$_2$CH$_2$— | chloroacetyl | |
| E-87 | 2-chloro-5-pyridyl | H | nitro | $+$CH$_2$CH$_2$C$\begin{matrix}\text{CH}_3\\-\\\text{CH}_3\end{matrix}$ | trichloroacetyl | |
| E-88 | 1,2,5-oxadiazol-3-yl | H | nitro | —(CH$_2$)$_3$— | 2,2-difluoropropionyl | |
| E-89a | 2-chloro-5-pyridyl | H | nitro | $\begin{matrix}\text{O}\\\|\\\text{OCCH}_2\text{Cl}\\-\text{CH}_2\text{CHCH}_2-\end{matrix}$ | chloroacetyl | |
| E-89b | 2-chloro-5-pyridyl | H | nitro | —CH$_2$CH$_2$— | bromoacetyl | mp. 200–203° C. (decomp.) |
| E-90 | 2-chloro-5-thiazolyl | H | nitro | —CH$_2$CH$_2$— | 1,1-dichloro-2,2-dimethylcyclopropylcarbonyl | |
| E-91 | 3-methyl-5-isooxazolyl | H | nitro | —CH$_2$CH$_2$— | acetyl | mp. 134–136° C. |
| E-92a | 2-chloro-5-pyridyl | H | nitro | —CH$_2$CH$_2$— | butyryl | mp. 137–140° C. |
| E-92b | 2-chloro-5-pyridyl | H | nitro | —(CH$_2$)$_3$— | valeryl | |
| E-93 | 5-thiazolyl | H | cyano | —CH$_2$CH$_2$— | trichloroacryloyl | |
| E-94 | 1,2,5-thiadiazol-3-yl | H | nitro | —CH$_2$CH$_2$— | methoxyacetyl | |
| E-95 | 5-pyrimidinyl | H | nitro | —CH$_2$CH$_2$— | cyanoacetyl | |
| E-96 | 2-fluoro-5-pyridyl | H | nitro | —(CH$_2$)$_3$— | 4-chlorobenzoyl | mp. 149–152° C. |
| E-97a | 2-chloro-5-pyridyl | H | cyano | —CH$_2$CH$_2$— | benzoyl | mp. 158–161° C. |
| E-97b | 2-bromo-5-pyridyl | H | nitro | —CH$_2$CH$_2$— | 2,6-difluorobenzoyl | |
| E-98 | 2-fluoromethyl-5-pyridyl | H | nitro | —CH$_2$CH$_2$— | 2-trifluoromethoxy-benzoyl | |
| E-99a | 3-pyridyl | H | cyano | —CH$_2$CH$_2$— | 2-fluoromethoxy-benzoyl | |
| E-99b | 2-chloro-5-thiazolyl | H | nitro | —CH$_2$CH$_2$— | 3-methylbenzoyl | mp. 146–148.5° C. (decomp.) |
| E-100 | 2-chloro-5-pyridyl | H | nitro | —(CH$_2$)$_3$— | 2,4-dichloro-5-thiazolylcarbonyl | |
| E-101 | 2-chloro-5-pyridyl | H | nitro | —(CH$_2$)$_3$— | 5-methyl-2-pyrimidinylcarbonyl | |
| E-102 | 1-ethyl-4-pyrazolyl | H | nitro | —(CH$_2$)$_3$— | 3-methyl-1,4-oxazin-2-yl-carbonyl | |
| E-103 | 2-chloro-5-pyridyl | methyl | nitro | —(CH$_2$)$_3$— | 5-nitro-2-furoyl | |
| E-104 | 4-isothiazolyl | H | nitro | —(CH$_2$)$_3$— | 2-naphthoyl | |

TABLE 2-continued

| Compound | W | R | Y | A | Z | Physical constant |
|---|---|---|---|---|---|---|
| E-105 | 2-methyl-5-thiazolyl | H | nitro | —CH$_2$CH$_2$— | 4,6-dichloro-1,3,5-triazin-2-yl-carbonyl | |
| E-106a | 2-chloro-5-pyridyl | H | nitro | —CH$_2$CH$_2$— | 2,4-dichloro-m-toluoyl | mp. 162–163° C. |
| E-106b | 2-chloro-5-pyridyl | H | nitro | —CH$_2$CH$_2$— | 2-furoyl | mp. 118–122° C. |
| E-107 | 2-chloro-5-pyridyl | H | nitro | —CH$_2$CH$_2$— | 2-chloro-5-pyridylcarbonyl | mp. 125–126° C. |
| E-108 | 2-chloro-5-pyridyl | H | nitro | —CH$_2$CH$_2$— | ethoxycarbonyl | $n_D^{20}$ 1.5880 |
| E-109 | 2-chloro-5-pyridyl | H | cyano | —CH$_2$CH$_2$— | ethoxycarbonyl | |
| E-110 | 2-methyl-5-pyridyl | methyl | nitro | —CH$_2$CH$_2$— | 2-methoxyethoxycarbonyl | |
| E-111 | 2-methyl-5-pyrazinyl | H | nitro | —CH$_2$CH$_2$— | 3-bromopropoxycarbonyl | |
| E-112 | 2-chloro-5-pyridyl | H | cyano | —(CH$_2$)$_3$— | n-hexyloxycarbonyl | |
| E-113 | 2-chloro-5-thiazolyl | H | nitro | —CH$_2$CH$_2$— | benzyloxycarbonyl | |
| E-114a | 2-chloro-5-pyridyl | H | nitro | —CH$_2$CH$_2$— | phenoxycarbonyl | mp. 135–140° C. |
| E-114b | 2-chloro-5-pyridyl | H | nitro | —CH$_2$CH$_2$— | benzyloxycarbonyl | $n_D^{50}$ 1.5986 |
| E-115 | 2-chloro-5-pyridyl | H | nitro | —CH$_2$CH$_2$— | 3,5,6-trichloro-2-pyridyl | |
| E-116 | 4-pyridyl | methyl | nitro | —CH$_2$CH$_2$— | isopropylthiocarbonyl | mp. 120–123° C. |
| E-117 | 1-methyl-4-pyrazolyl | H | nitro | —(CH$_2$)$_3$— | phenylthiocarbonyl | |
| E-118 | 2-chloro-5-pyridyl | H | nitro | —CH$_2$CH$_2$— | methylaminocarbonyl | |
| E-119 | 2-chloro-5-pyridyl | H | nitro | —CH$_2$CH$_2$— | 3-chloroanilinocarbonyl | mp. 186–188° C. |
| E-120 | 2-chloro-5-thiazolyl | H | cyano | —CH$_2$CH$_2$— | allylaminocarbonyl | |
| E-121 | 2-bromo-5-pyridyl | H | nitro | —CH$_2$CH$_2$— | propargylaminocarbonyl | |
| E-122 | 2-chloro-5-pyridyl | H | nitro | —CH$_2$CH$_2$— | dimethylaminocarbonyl | |
| E-123 | 2-chloro-5-pyridyl | H | nitro | —CH$_2$CH$_2$— | diethylaminocarbonyl | |
| E-124 | 3-pyridyl | H | nitro | —(CH$_2$)$_3$— | 2-methylpiperidinocarbonyl | mp. 191–192° C. |
| E-125 | 2-fluoro-5-pyrimidinyl | H | nitro | —CH$_2$CH$_2$— | N—methylanilinocarbonyl | |
| E-126 | 2-chloro-5-pyridyl | H | nitro | —CH$_2$CH$_2$— | methylsulfonyl | |
| E-127 | 5-chloro-2-pyridyl | H | nitro | —CH$_2$CH$_2$— | chloromethylsulfonyl | |
| E-128 | 2-chloro-5-pyridyl | H | cyano | —CH$_2$CH$_2$— | tosyl | |
| E-129 | 3-methyl-5-isooxazolyl | H | nitro | —CH$_2$CH$_2$— | methylsulfonyl | mp. 156–158° C. |
| E-130 | 3-methyl-5-isooxazolyl | H | nitro | —CH$_2$CH$_2$— | 2-methyl-5-nitro-phenylsulfonyl | mp. 154–156° C. |
| E-131 | 2-fluoro-5-pyridyl | H | nitro | —CH$_2$CH$_2$— | methoxysulfonyl | |
| E-132 | 2-chloro-5-pyridyl | H | nitro | —CH$_2$CH$_2$— | dimethylaminosulfonyl | |
| E-133 | 2-chloro-5-pyridyl | H | nitro | —CH$_2$CH$_2$— | O,O—dimethylphosphono | $n_D^{24}$ 1.5760 |
| E-134 | 2-chloro-5-pyridyl | H | cyano | —CH$_2$CH$_2$— | O—ethyl-S—propylthio-phosphono | $n_D^{20}$ 1.5615 |
| E-135 | 1-methyl-4-pyrazolyl | H | nitro | —(CH$_2$)$_3$— | O—ethyl-S—propyl-dithiophosphono | |
| E-136 | 2-chloro-5-thiazolyl | H | nitro | —CH$_2$CH$_2$— | 2-cyanoethyl | $n_D^{20}$ 1.6176 |
| E-137 | 2-chloro-5-thiazolyl | H | cyano | —CH$_2$CH$_2$— | 3,3-dimethyl-2-butanon-1-yl | $n_D^{20}$ 1.5446 |
| E-138 | 2-chloro-5-pyridyl | H | nitro | —CH$_2$CH$_2$— | cyano | mp. 122–126° C. |
| E-139 | 2-chloro-5-thiazolyl | H | nitro | —CH$_2$CH$_2$— | methoxy-carbonyl | |
| E-140 | 2-chloro-5-pyridyl | H | nitro | —CH$_2$CH$_2$— | | mp. 176–180° C. (decomp.) |
| E-141 | 2-chloro-5-pyridyl | H | nitro | —CH$_2$CH$_2$— | | mp. 128–131° C. |

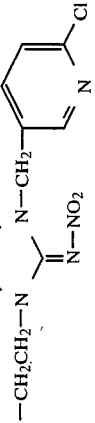

TABLE 2-continued

| Compound | W | R | Y | A | Z | Physical constant |
|---|---|---|---|---|---|---|
| E-142 | 2-chloro-5-pyridyl | H | nitro | —CH₂CH₂— | cyano | mp. 85-87° C. |
| E-143 | 2-chloro-5-pyridyl | H | nitro | —CH₂CH₂— | chloroacetyl | mp. 134-136° C. |
| E-144 | 2-chloro-5-pyridyl | H | nitro | —CH₂CH₂— | pivaloyl | mp. 186-187° C. |
| E-145 | 2-chloro-5-pyridyl | H | nitro | —CH₂CH₂— | 3-cyanobenzyl | mp. 154-158° C. |
| E-146 | 2-chloro-5-pyridyl | H | nitro | —CH₂CH₂— | pentafluorobenzyl | mp. 166-170° C. |
| E-147 | 2-chloro-5-pyridyl | H | nitro | —CH₂CH₂— | pentafluorobenzoyl | mp. 168-169° C. |
| E-148 | 2-chloro-5-pyridyl | H | nitro | —CH₂CH₂— | 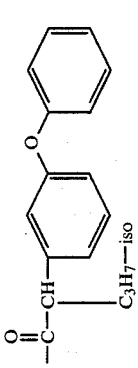 | mp. 181-185° C. |
| E-149 | 2-chloro-5-pyridyl | H | nitro | —CH₂CH₂— | 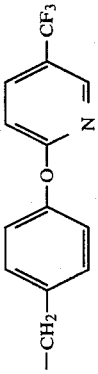 | $n_D^{20}$ 1.5880 |
| E-150 | 2-chloro-5-pyridyl | H | nitro | —CH₂CH₂— | ethoxycarbonylmethyl | mp. 148-151° C. |
| E-151 | 2-chloro-5-pyridyl | H | cyano | —CH₂CH₂— | cyano | mp. 133-134° C. |
| E-152 | 2-chloro-5-thiazolyl | H | nitro | —CH₂CH₂— | cyano | $n_D^{20}$ 1.6176 |

Example 6

(biological test)

Test on organophosphate-resistant green rice leafhoppers (*Nephotettix cincticeps*):

Preparation of a test chemical

Solvent: 3 parts by weight of xylene

Emulsifier: 1 part by weight of polyoxyethylene alkylphenyl ether

To produce a suitable preparation of active compound, 1 part by weight of the active compound was mixed with the stated amount of solvent and the stated amount of emulsifier, and the mixture was diluted with water to a predetermined concentration.

Testing method

A water dilution of each of the active compounds in a predetermined concentration prepared as above was sprayed onto rice plants, about 10 cm tall, grown in pots having a diameter of 12 cm at a rate of 10 ml per pot. The sprayed chemical was dried, and a wire net having a diameter of 7 cm and a height of 14 cm was put over each of the pots, and 30 female imagoes of rice leafhopper (*Nephotettix cincticeps*) of a strain having resistance to organophosphate chemicals were released into the net. The pots were placed in a constant-temperature chamber. Two days later, the number of dead insects was examined, and the kill ratio was calculated.

Example 7

(biological test)

Test on organophosphate-resistant white-backed planthopper (*Sogattella furcifera*):

Testing method

A water dilution of each of the active compounds in a predetermined concentration prepared as in the preceding Example was sprayed onto rice plants, 10 cm tall, grown in pots having a diameter of 12 cm at a rate of 10 ml per pot. The sprayed chemical was dried, and a wire net having a diameter of 7 cm and a height of 14 cm was put over each of the pots, and 30 female imagoes of white-backed planthopper (*Sogatella furcifera*) of a strain having resistance to organophosphate chemicals were released into the net and the pots were placed in a constant temperature chamber. Two days later, the number of dead insects was examined, and the kill ratio was calculated.

Results:

In the biological tests mentioned above (Examples 6 and 7) it has been found that the active compounds, shown in Table 2, have an excellent insecticidal effect at a concentration of 200 ppm, and also have a good insecticidal effect even in a concentration lower than 200 ppm.

It will be appreciated that the instant specification and examples are set forth by way of illustration and not limitation, and that various modifications and changes may be made without departing from the spirit and scope of the present invention.

What is claimed is:

1. A compound selected from the group consisting of 1-cyclopropyl-2-nitroiminoimidazolidine of the formula:

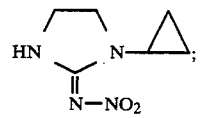

1-(2-chloroethyl)-2-nitroiminoimidazolidine of the formula:

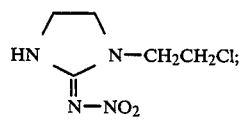

1-[2-(4-chlorophenoxy)ethyl]-2-nitroiminoimidazolidine of the formula:

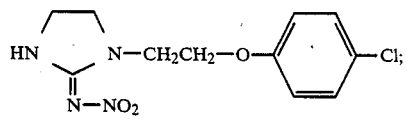

1-(3-methylthiopropyl)-2-nitroiminoimidazolidine of the formula:

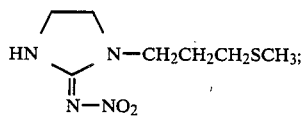

1-(2-cyanoethyl)-2-nitroiminoimidazolidine of the formula:

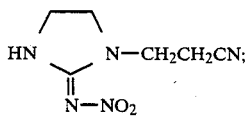

1-(3-cyanopropyl)-2-cyanoiminoimidazolidine of the formula:

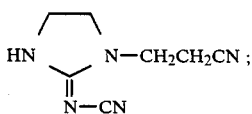

1-(3,3-dimethyl-2-butanon-1-yl)-2-cyanoiminoimidazolidine of the formula:

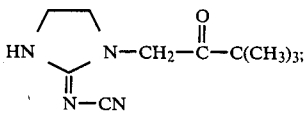

1-(3,3-dimethyl-2-butanon-1-yl)-2-nitroiminoimidazolidine of the formula:

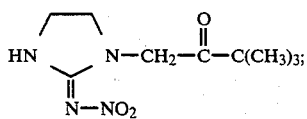

2-nitroimino-1-(3-pyridylcarbonylmethyl)imidazolidine of the formula:

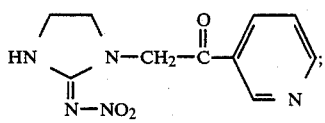

2-cyanoimino-1-ethoxycarbonylmethyltetrahydropyrimidine of the formula:

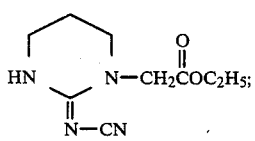

1-[2-(O-ethyl-S-propylthiophosphonoxy)ethyl]-2-nitroiminoimidazolidine of the formula:

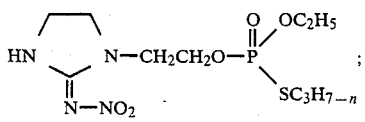

2-nitroimino-1-trimethylsilylmethylimidazolidine of the formula:

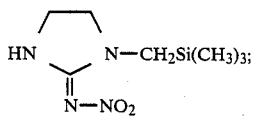

2-nitroimino-1-(2-thiazolyl)imidazolidine of the formula:

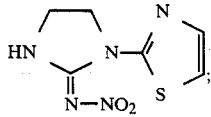

2-nitroimino-1-propylcarbonylimidazolidine of the formula:

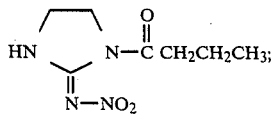

2-cyanoimino-1-cyclopropylcarbonyltetrahydropyrimidine of the formula:

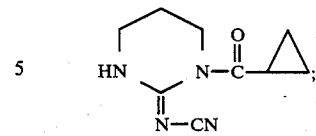

1-bromoacetyl-2-nitroiminoimidazolidine of the formula:

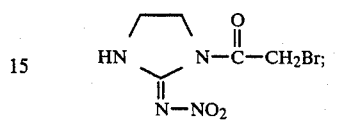

2-cyanoimino-1-trichloroacryloylimidazolidine of the formula:

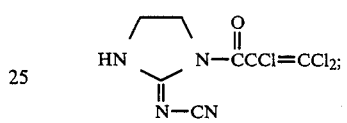

1-(2-methoxyethoxycarbonyl)-2-nitroiminoimidazolidine of the formula:

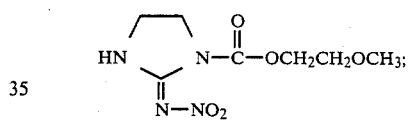

1-benzyloxycarbonyl-2-nitroiminoimidazolidine of the formula:

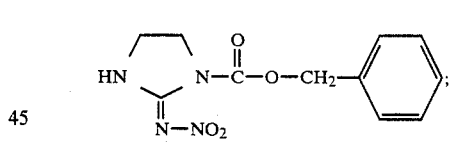

1-ethylaminocarbonyl-2-nitroiminoimidazolidine of the formula:

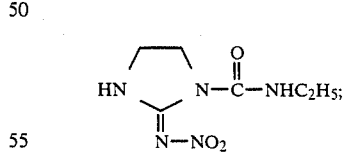

1-dimethylaminocarbonyl-2-nitroiminoimidazolidine of the formula:

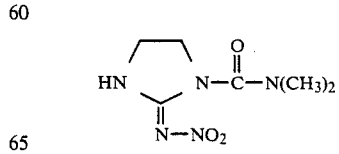

1-methylsulfonyl-2-nitroiminoimidazolidine of the formula:

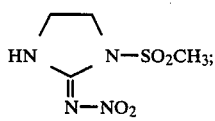

2-nitroimino-1-phenylsulfonyltetrahydropyrimidine of the formula:

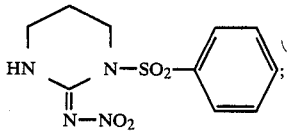

1-(O,O-dimethylphosphono)-2-nitroiminoimidazolidine of the formula:

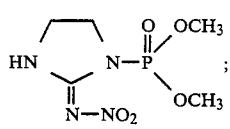

1-(O-ethyl-S-propylthiophosphono)-2-nitroiminoimidazolidine of the formula:

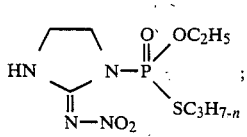

1-(2,4-dichlorobenzoyl)-2-nitroiminoimidazolidine of the formula:

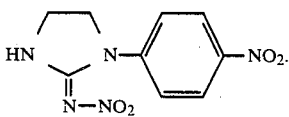

1-(3,5-dichlorobenzoyl)-2-cyanoiminoimidazolidine of the formula:

1-(2-furoyl)-2-nitroiminoimidazolidine of the formula:

2. 1-(4-Nitrophenyl)-2-nitroiminoimidazolidine of the formula

* * * * *